United States Patent [19]

MacPherson et al.

[11] Patent Number: 5,244,889
[45] Date of Patent: Sep. 14, 1993

[54] CERTAIN MACROCYCLIC LACTAM DERIVATIVES

[75] Inventors: Lawrence J. MacPherson, Hampton; James L. Stanton, Lebanon, both of N.J.

[73] Assignee: Ciba-Geigy Corporation, Ardsley, N.Y.

[21] Appl. No.: 798,684

[22] Filed: Nov. 26, 1991

[51] Int. Cl.$^5$ ............... C07D 281/00; C07D 267/00; A61K 31/395
[52] U.S. Cl. .................................... 514/183; 540/454
[58] Field of Search ...................... 540/454; 514/183

[56] References Cited

U.S. PATENT DOCUMENTS

| | | | |
|---|---|---|---|
| 5,075,302 | 12/1991 | Neu Stadt | 574/211 |
| 5,095,110 | 3/1992 | Flynn et al. | 540/522 |

FOREIGN PATENT DOCUMENTS

| | | | |
|---|---|---|---|
| 0049842 | 4/1982 | European Pat. Off. | 540/451 |
| 322633 | 7/1989 | European Pat. Off. | 562/2 |
| 2141120 | 12/1984 | United Kingdom | 540/454 |
| 9105796 | 5/1991 | World Int. Prop. O. | 560/121 |
| 9113870 | 9/1991 | World Int. Prop. O. | 546/243 |

OTHER PUBLICATIONS

Trends Pharmacol. Sci., vol. 11, No. 6, 1990 pp. 245–249 Roques et al.
Tidia Research Fonndation Symposium Series, vol. 2, 1989, pp. 47–54 Indos et al.
Clinical Nephrology, vol. 36, No. 4, 1991, pp. 187–191, Sybertz.
Medicinal Research Reviews, vol. 5, No. 4 pp. 483–531 (1985).
Bill Chemical Biophys. Res. Comm III, 166 (1983).
S. Am. Chem Soc. 112, 327 (1990).

Primary Examiner—Robert T. Bond
Attorney, Agent, or Firm—Norbert Gruenfeld

[57] ABSTRACT

The invention relates to macrocyclic lactam derivatives of formula I

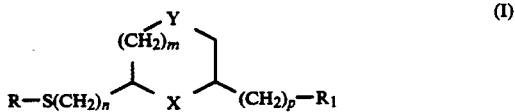

wherein R is hydrogen or acyl; m is an integer from 4 to 9 inclusive; n is 1 or 2; p is zero, 1 or 2; X is —CONH— or —NHCO—; Y is S, O or $CH_2$; $R_1$ is —COOH; or $R_1$ is

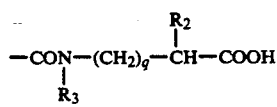

in which $R_2$ is hydrogen, lower alkyl, aryl-lower alkyl, amino-lower alkyl, hydroxy-lower alkyl, acyloxy-lower alkyl, lower alkoxy-lower alkyl, mercapto-lower alkyl, lower alkyl-(thio, sulfinyl or sulfonyl)-lower alkyl, or carboxy-lower alkyl, $R_3$ is hydrogen or lower alkyl, and q is zero or an integer from 1 to 5 inclusive; or $R_1$ is

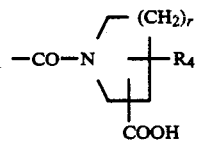

in which $R_4$ is hydrogen, lower alkyl, lower alkoxy, hydroxy or acyloxy, and r is 1 or 2; or $R_1$ is

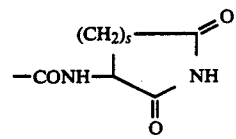

in which s is 1 or 2; or $R_1$ is (Abstract continued on next page.)

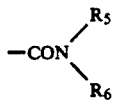

in which $R_5$ and $R_6$ independently represent hydrogen, lower alkyl, $C_5$- or $C_6$-cycloalkyl, (hydroxy-, acyloxy or lower alkoxy-) lower alkyl, carbocyclic or heterocyclic monocyclic aryl, or (hydroxy-, acyloxy- or alkoxy-) lower alkyloxy-lower alkyl; or $R_5$ and $R_6$ together with the nitrogen to which they are attached represent pyrrolidino, piperidino, morpholino, piperazino or N-alkyl-piperazino; and macrocyclic sulfur and oxygen containing lactam ring isomers in which a $CH_2$ group of $(CH_2)_m$ in formula I is replaced by O or S, and Y represents $CH_2$; and pharmaceutically acceptable prodrug esters of any above said compound with a free carboxyl group; and pharmaceutically acceptable salts of any said compounds with a free acid or basic salt forming group; pharmaceutical compositions comprising said compounds; methods for the preparation of said compounds and for the preparation of intermediates; and methods of treating disorders in mammals which are responsive to the inhibition of neutral endopeptidases by administration of said compounds to mammals in need of such treatment.

12 Claims, No Drawings

CERTAIN MACROCYCLIC LACTAM DERIVATIVES

SUMMARY OF THE INVENTION

Endogenous atrial natriuretic peptides (ANP), also called atrial natriuretic factors (ANF), have diuretic, natriuretic and vasorelaxant functions in mammals. The natural ANF peptides are metabolically inactivated, in particular by a degrading enzyme which has been recognized to correspond to the enzyme neutral endopeptidase (NEP) EC 3.4. 24.11, also responsible for e.g. the metabolic inactivation of enkephalins.

The aim of the present invention is to provide novel macrocyclic lactam derivatives described below which are useful as neutral endopeptidase (NEP) inhibitors, e.g. as inhibitors of the ANF-degrading enzyme in mammals, so as to prolong and potentiate the diuretic, natriuretic and vasodilator properties of ANF in mammals, by inhibiting the degradation thereof to less active metabolites. The compounds of the invention are thus particularly useful for the treatment of conditions and disorders responsive to the inhibition of neutral endopeptidase EC 3.4. 24.11, particularly cardiovascular disorders, such as hypertension, renal insufficiency including edema and salt retention, cyclosporin induced renal toxicity, pulmonary edema and congestive heart failure. By virtue of their inhibition of neutral endopeptidase, the compounds of the invention may also be useful for the treatment of pain, depression and certain psychotic conditions. Other potential indications include the treatment of angina, premenstrual syndrome, Meniere's disease, hyperaldosteronism, hypercalciuria, ascites, glaucoma, asthma and gastrointestinal disorders such as diarrhea, irritable bowel syndrome and gastric hyperacidity.

DETAILED DESCRIPTION OF THE INVENTION

The present invention relates to the macrocyclic lactam derivatives of formula I

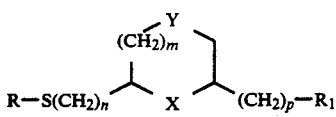
(I)

wherein R is hydrogen or acyl; m is an integer from 4 to 9 inclusive; n is 1 or 2; p is zero, 1 or 2; X is —CONH— or —NHCO—; Y is S, O or $CH_2$; $R_1$ is —COOH; or $R_1$ is

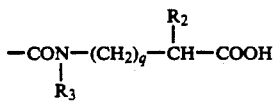
(a)

in which $R_2$ is hydrogen, lower alkyl, aryl-lower alkyl, amino-lower alkyl, hydroxy-lower alkyl, acyloxy-lower alkyl, lower alkoxy-lower alkyl, mercapto-lower alkyl, lower alkyl-(thio, sulfinyl or sulfonyl)-lower alkyl, or carboxy-lower alkyl, $R_3$ is hydrogen or lower alkyl, and q is zero or an integer from 1 to 5 inclusive; or $R_1$ is

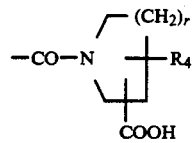
(b)

in which $R_4$ is hydrogen, lower alkyl, lower alkoxy, hydroxy or acyloxy, and r is 1 or 2; or $R_1$ is

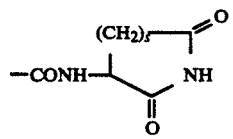
(c)

in which s is 1 or 2; or $R_1$ is

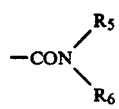
(d)

in which $R_5$ and $R_6$ independently represent hydrogen, lower alkyl, $C_5$- or $C_6$-cycloalkyl, (hydroxy-, acyloxy or lower alkoxy-) lower alkyl, carbocyclic or heterocyclic monocyclic aryl, or (hydroxy-, acyloxy- or alkoxy-) lower alkyloxy-lower alkyl; or $R_5$ and $R_6$ together with the nitrogen to which they are attached represent pyrrolidino, piperidino, morpholino, piperazino or N-alkylpiperazino; and macrocyclic sulfur and oxygen containing lactam ring isomers in which a $CH_2$ group of $(CH_2)_m$ in formula I is replaced by O or S, and Y represents $CH_2$; pharmaceutically acceptable esters of any above said compounds with a free carboxyl group; and pharmaceutically acceptable salts of any said compounds with a free acid or basic salt forming group; pharmaceutical compositions comprising said compounds; methods for the preparation of said compounds and for the preparation of intermediates; and methods of treating disorders in mammals which are responsive to the inhibition of neutral endopeptidases by administration of said compounds to mammals in need of such treatment.

Pharmaceutically acceptable ester derivatives are preferably prodrug derivatives, such being convertible by solvolysis or under physiological conditions to the free carboxylic acids of formula I.

Compounds of formula I and derivatives thereof, depending on the nature of substituents, possess one or more asymmetric carbon atoms. The resulting geometric isomers, diastereomers, racemates and optical antipodes are encompassed by the instant invention.

To the extent that certain compounds of the invention may be derived from natural amino acids, the configuration at the corresponding asymmetric centers is preferably that of the natural (L)-amino acids involved; the asymmetric carbon atom corresponding to that of the natural α-amino acids is normally in the (S)-configuration; it is in the (R)-configuration in the case of cysteine derivatives.

Specific embodiments of the invention relate to the compounds of the invention wherein in formula I
(a) X is —CONH—;
(b) X is —NHCO—;
(c) Y is $CH_2$;

(d) Y is O or S;
(e) n is one;
(f) X is -CONH-, p is zero and n is one;
(g) X is -NHCO-, p is one and n is one;
(h) m is 4;
(i) m is 7;
(j) m is 8.

More particularly, the invention relates to compounds of fromula II

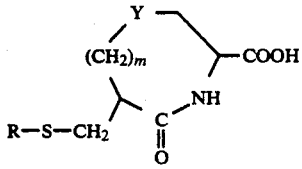
(II)

wherein R represents hydrogen or acyl; m is an integer from 4 to 9 inclusive; Y is CH$_2$ or S; pharmaceutically acceptable esters thereof; and pharmaceutically acceptable salts thereof.

Preferred are said compounds of formula II and ester derivatives wherein m is 4, 7 or 8 and Y is CH$_2$ or S. Further preferred are said compounds wherein Y is CH$_2$, also said compounds wherein m is 4.

The invention also relates more particularly to the compounds of formula III

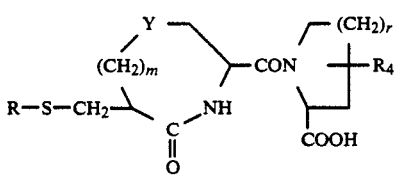
(III)

wherein m is an integer from 4 to 9 inclusive; Y is CH$_2$ or S; r is 1 or 2; R is hydrogen or acyl; R$_4$ is hydrogen, lower alkyl, lower alkoxy, hydroxy or acyloxy; and pharmaceutically acceptable esters thereof; and pharmaceutically acceptable salts thereof.

Preferred are said compounds of formula III and derivatives thereof wherein m is 4, 7 or 8; Y is CH$_2$; r is one; and R and R$_4$ have meaning as defined above. Further preferred are said compounds wherein m is 4, Y is CH$_2$, r is one; and R$_4$ is hydroxy or acyloxy, advantageously at the 4-position.

The invention further relates preferably to the particular compounds of formula IV

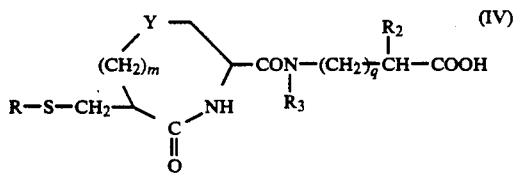
(IV)

wherein m is an integer from 4 to 9 inclusive; q is zero or an interger of 1 to 5; Y is CH$_2$ or S; R is hydrogen or acyl; R$_2$ is hydrogen, lower alkyl, aryl-lower alkyl, amino-lower alkyl, hydroxy-lower alkyl, acyloxy-lower alkyl, alkoxy-lower alkyl, mercapto-lower alkyl, lower alkyl-(thio, sulfinyl or sulfonyl)-lower alkyl or carboxy-lower alkyl; R$_3$ is hydrogen or lower alkyl; and pharmaceutically acceptable esters thereof; and pharmaceutically acceptable salts thereof.

Preferred are said compounds of formula IV and derivatives therein wherein Y is CH$_2$; R$_3$ is hydrogen; q is zero; and R, m and R$_2$ have meaning as defined above. Further preferred are said compounds wherein Y is CH$_2$; R$_3$ is hydrogen; m is 4, 7 or 8; q is zero; and R and R$_2$ have meaning as defined above.

The invention further relates to the compounds of formula V

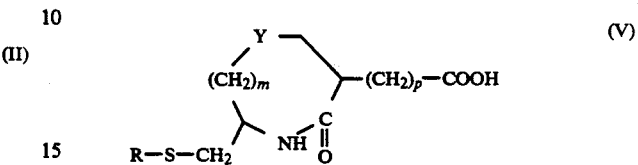
(V)

wherein Y is CH$_2$; R is hydrogen or acyl; m is an integer from 4 to 9 inclusive; p is zero, one or two; and pharmaceutically acceptable esters thereof; and pharmaceutically acceptable salts thereof.

Preferred are said compounds of formula V and derivatives where p is one; and Y, m and R have meaning as defined above. Further preferred are said compounds wherein p is one, m is 4, and R has meaning as defined above.

Further embodiments of the invention relate to the compounds cited hereinabove wherein the macrocyclic ring substituents are either cis or trans.

A particular embodiment of the invention relates to the compounds of formula I wherein X is —CONH—, namely the trans compounds of formula Ia

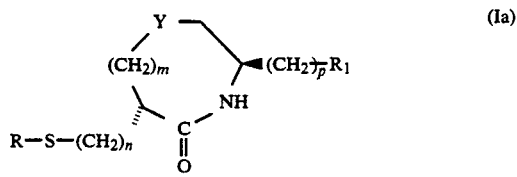
(Ia)

wherein R, R$_1$, n, m, p and Y have meaning as defined above in formula I, particularly said compounds wherein p is zero and n is one, and pharmaceutically acceptable esters and salts thereof.

Preferred are the said trans compounds corresponding to formula II, III and IV wherein m is 4, and pharmaceutically acceptable esters and salts thereof.

Lactam macrocyclic ring isomers of the sulfur and oxygen ring containing compounds of formula I, Ia, II, III, IV and V (wherein Y represents O or S), and ester derivatives and salts thereof, are preferably the isomers wherein the CH$_2$ group of (CH$_2$)$_m$ directly adjacent to Y is replaced by O or S and Y represents CH$_2$.

The definitions used herein, unless denoted otherwise, have the following meanings within the scope of the present invention.

Aryl represents carbocyclic or heterocyclic aryl, preferably carbocyclic aryl.

Carbocyclic aryl preferably represents preferably monocyclic carbocyclic aryl or optionally substituted naphthyl.

Monocyclic carbocyclic aryl represents optionally substituted phenyl, being preferably phenyl or phenyl substituted by one to three substituents, such being advantageously lower alkyl, hydroxy, lower alkoxy, lower alkanoyloxy, halogen, cyano, trifluoromethyl, lower alkanoylamino or lower alkoxycarbonyl.

Optionally substituted naphthyl represents 1- or 2-naphthyl or 1- or 2-naphthyl preferably substituted by lower alkyl, lower alkoxy or halogen.

Heterocyclic aryl represents preferably monocyclic heterocyclic aryl such as optionally substituted thienyl, furanyl, pyridyl, pyrrolyl or N-lower alkylpyrrolyl.

Optionally substituted furanyl represents 2- or 3-furanyl or 2- or 3-furanyl preferably substituted by lower alkyl.

Optionally substituted pyridyl represents 2-, 3- or 4-pyridinyl or 2-, 3- or 4-pyridyl preferably substituted by lower alkyl, halogen or cyano.

Optionally substituted thienyl represents 2- or 3-thienyl or 2- or 3-thienyl preferably substituted by lower alkyl.

Aryl in aryl-lower alkyl is preferably phenyl or phenyl substituted by one or two of lower alkyl, lower alkoxy, hydroxy, lower alkanoyloxy, halogen, trifluoromethyl, cyano, lower alkanoylamino or lower alkoxycarbonyl.

The term "lower" referred to herein in connection with organic radicals or compounds respectively defines such with up to and including 7, preferably up to and including 4 and advantageously one or two carbon atoms. Such may be straight chain or branched.

A lower alkyl group preferably contains 1–4 carbon atoms and represents for example ethyl, propyl, butyl or advantageously methyl.

A lower alkoxy group preferably contains 1–4 carbon atoms and represents for example methoxy, propoxy, isopropoxy or advantageously ethoxy.

Aryl-lower alkyl is advantageously benzyl or phenethyl optionally substituted by one or two of lower alkyl, lower alkoxy, hydroxy, lower alkanoyloxy, halogen or trifluoromethyl.

$C_1$–$C_{20}$-Alkyl represents branched or unbranched alkyl with 1 to 20 carbon atoms.

The term $C_5$–$C_7$-cycloalkyl represents a saturated cyclic hydrocarbon radical which preferably contains 5 to 7 ring carbons and is, preferably cyclopentyl or cyclohexyl.

The term cycloalkyl(lower)alkyl represents preferably 1- or 2-(cyclopentyl or cyclohexyl)ethyl, 1-, 2- or 3-(cyclopentyl or cyclohexyl)propyl, or 1-, 2-, 3- or 4-(cyclopentyl or cyclohexyl)-butyl.

Amino-lower alkyl represents preferably amino-(ethyl, propyl or butyl), particularly omega-amino-(ethyl, propyl or butyl).

A di-lower alkylamino group preferably contains 1–4 carbon atoms in each lower alkyl portion and represents, for example, N,N-dimethylamino, N-methyl-N-ethylamino and advantageously N,N-diethylamino.

A lower alkoxycarbonyl group preferably contains 1 to 4 carbon atoms in the alkoxy portion and represents, for example, methoxycarbonyl, propoxycarbonyl, isopropoxycarbonyl or advantageously ethoxycarbonyl.

A lower alkyl-(thio, sulfinyl or sulfonyl)-lower alkyl group represents for example lower alkyl-(thio, sulfinyl or sulfonyl)-methyl.

Lower alkoxycarbonyl-lower alkoxy represents advantageously e.g. 1-(ethoxycarbonyl)ethoxy or ethoxycarbonylmethoxy.

Di(lower)alkylamino-lower alkoxy advantageously represents diethylaminoethoxy.

Hydroxy-lower alkyl is preferably hydroxymethyl.

Carboxy-lower alkyl is for example carboxymethyl or carboxyethyl.

Halogen (halo) preferably represents fluoro or chloro, but may also be bromo or iodo.

Acyl represents lower alkanoyl, carbocyclic aryl-lower alkanoyl, aroyl, lower alkoxycarbonyl or aryl-lower alkoxycarbonyl, advantageously lower alkanoyl. Lower alkoxycarbonyl for acyl is preferably t-butoxycarbonyl (abbreviated t-BOC). Aryl-lower alkoxycarbonyl for acyl is preferably benzyloxycarbonyl (abbreviated CBZ).

Acyloxy is preferably lower alkanoyloxy or aroyloxy.

Lower alkanoyl is preferably acetyl, propionyl, butyryl, or pivaloyl.

Lower alkanoyloxy is preferably acetoxy, pivaloyloxy or propionyloxy.

Acylamino represents preferably lower alkanoylamino, aroylamino, or aryl-lower alkoxycarbonylamino such as benzyloxycarbonylamino.

Lower alkanoylamino is preferably acetamido or propionamido.

Aroyl is preferably benzoyl or benzoyl substituted on the benzene ring by lower alkyl, lower alkoxy, halogen or trifluoromethyl.

Pharmaceutically acceptable esters of the carboxylic acids of the invention are preferably those wherein any free carboxyl group present in the compounds cited herein is derivatized as a prodrug ester group.

Carboxyl derivatized as a pharmaceutically acceptable prodrug ester group, represents an ester group that may be convertible by solvolysis or under physiological conditions to the free carboxylic acid, such being preferably $C_1$–$C_{20}$-alkoxycarbonyl, advantageously lower alkoxycarbonyl; (amino, acylamino, mono- or di-lower alkylamino)-lower alkoxycarbonyl; carboxy-lower alkoxycarbonyl, e.g. alpha-carboxy-lower alkoxycarbonyl; lower alkoxycarbonyl-lower alkoxycarbonyl, e.g. alpha-lower alkoxycarbonyl-lower alkoxycarbonyl; α-(di-lower alkylamino, amino, mono-lower alkylamino, morpholino, piperidino, pyrrolidino, 1-lower alkylpiperazino)-carbonyl-lower alkoxycarbonyl; aryl-lower alkoxycarbonyl, preferably optionally (halo, lower alkyl or lower alkoxy)-substituted benzyloxycarbonyl, or pyridyl-methoxycarbonyl; 1-(hydroxy, lower alkanoyloxy or lower alkoxy)-lower alkoxycarbonyl, e.g. pivaloyloxymethoxycarbonyl; (hydroxy, lower alkanoyloxy or lower alkoxy)-lower alkoxymethoxycarbonyl; bicycloalkoxycarbonyl-lower alkoxycarbonyl, e.g. bicyclo-[2,2,1]-heptyloxycarbonyl-lower alkoxycarbonyl, especially bicyclo-[2,2,1]-heptyloxycarbonyl-methoxycarbonyl such as bornyloxycarbonylmethoxycarbonyl; 1-(lower alkoxycarbonyloxy)-lower alkoxycarbonyl; 5-indanyloxycarbonyl; 3-phthalidoxycarbonyl and (lower alkyl, lower alkoxy or halo)-substituted 3-phthalidoxycarbonyl; dihydroxypropyloxycarbonyl wherein hydroxy groups are free or are protected in the form of ketals, e.g. a lower alkylidene, a benzylidene or a 5- or 6-membered cycloalkylidene derivative, advantageously being (2,2-dimethyl-1,3-dioxolan-4-yl)-methoxycarbonyl.

Carboxyl derivatized as a pharmaceutically acceptable prodrug ester group represents most advantageously $C_1$–$C_4$-alkoxycarbonyl, benzyloxycarbonyl optionally substituted on phenyl by lower alkyl, lower alkoxy, halo or trifluoromethyl, 1-($C_2$–$C_4$-alkanoyloxy)ethoxycarbonyl, (2,2-dimethyl-1,3-dioxolan-4-yl)-methoxycarbonyl, 5-indanyloxycarbonyl, 1-($C_1$–$C_4$-alkoxycarbonyloxy)-ethoxycarbonyl, or 3-pyridylmethoxycarbonyl.

Pharmaceutically acceptable salts are either pharmaceutically acceptable acid addition salts for any basic compounds of the invention or salts derived from pharmaceutically acceptable bases for any acidic compounds of the invention.

Pharmaceutically acceptable salts of basic compounds of the invention are acid addition salts, which are preferably such of therapeutically acceptable inorganic or organic acids, such as strong mineral acids, for example hydrohalic, e.g. hydrochloric or hydro-bromic acid, sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, 1,2-ethanedisulfonic acid, benzenesulfonic, p-toluenesulfonic, naphthalenesulfonic, sulfanilic, cyclohexylsulfamic acid, or ascorbic acid.

Pharmaceutically acceptable salts of the acidic compounds of the invention, e.g. those having a free carboxyl group are salts formed with pharmaceutically acceptable bases, e.g. alkali metal salts (e.g. sodium, potassium salts), alkaline earth metal salts (e.g. magnesium, calcium salts), amine salts (e.g. ethanolamine, diethanolamine, triethanolamine, tromethamine salts).

The novel compounds of the invention are pharmacologically potent neutral endopeptidase (NEP) enzyme inhibitors which inhibit e.g. the degradation of atrial natriuretic factors (ANF) in mammals. They thus potentiate e.g. the diuretic and natriuretic effect of exogenous or endogenous ANF in mammals.

The compounds of the invention are thus particularly useful in mammals as diuretic, natriuretic (saluretic) and antihypertensive agents for the treatment of e.g. hypertension, congestive heart failure and edema.

As neutral endopeptidase inhibitors, the compounds are also e.g. enkephalinase inhibitors so as to inhibit the degradation of endogenous enkephalins and may thus also be useful for the treatment of pain in mammals.

The above-cited properties are demonstrable in vitro and in vivo tests, using advantageously mammals, e.g. mice, rats, dogs, monkeys or isolated organs, tissues and preparations thereof. Said compounds can be applied in vitro in the form of solutions, e.g. preferably aqueous solutions, and in vivo either enterally, parenterally, advantageously intravenously, e.g. as a suspension or in aqueous solution. The dosage in vitro may range between about $10^{-4}$ molar and $10^{-9}$ molar concentrations. The dosage in vivo may range depending on the route of administration, between about 0.1 and 50 mg/kg, advantageously between about 1.0 and 30 mg/kg.

The analgesic activity can be determined by measuring the potentiation of the analgesic effects of enkephalin and derivatives thereof, and by classical analgesic tests, such as the phenyl-p-benzoquinone induced writhing test [J. Pharmacol. Exp. Therap. 125, 237 (1959)] and the hot plate test in the mouse [J. Pharmacol. Exp. Therap. 107, 385 (1953)].

The antihypertensive activity can be determined in the spontaneously hypertensive rat, Goldblatt rat or Goldblatt dog by direct measurement of blood pressure. Advantageously, the effect is measured in the DOCA-salt hypertensive rat and/or renal hypertensive rat or dog model.

Certain compounds of the invention further exhibit angiotensin converting enzyme (ACE) inhibitory activity also indicative of useful antihypertensive and cardiac effects in mammals.

The diuretic (saluretic) activity can be determined in standard diuretic screens, e.g. as described in "New Antihypertensive Drugs", Spectrum Publications, 1976, pages 307-321, or by measuring the potentiation of atrial natriuretic factor-induced natriuresis and diuresis in the rat.

The potentiation of ANF can also be determined by measuring the increase in ANF plasma level achieved.

The in vitro inhibition of neutral endopeptidase (NEP) 3.4.24.11 can be determined as follows:

Neutral endopeptidase 3.4.24.11 activity is determined by the hydrolysis of the substrate glutaryl-Ala-Ala-Phe-2-naphthylamide (GAAP) using a modified procedure of Orlowski and Wilk (1981). The incubation mixture (total volume 125 $\mu$l) contains 4.2 $\mu$g of protein (rat kidney cortex membranes prepared by method of Maeda et al, 1983), 50 mM tris buffer, pH 7.4 at 25° C., 500 $\mu$M substrate (final concentration), and leucine aminopeptidase M (2.5 $\mu$g). The mixture is incubated for 10 minutes at 25° C. and 100 $\mu$l of fast garnet (250 $\mu$g fast garnet/ml of 10% Tween 20 in 1M sodium acetate, pH 4.2) is added. Enzyme activity is measured spectrophotometrically at 540 nm. One unit of NEP 24.11 activity is defined as 1 nmol of 2-naphthylamine released per minute at 25° C. at pH 7.4 $IC_{50}$ values for inhibition of the enzyme are determined, i.e. the concentration of test compound required for 50% inhibition of the release of 2-naphthylamine.

Neutral endopeptidase activity is also determined using ANF as a substrate. A trial natriuretic factor degrading activity is determined by measuring the disappearance of rat-ANF (r-ANF) using a 3 minute reverse phase-HPLC separation. An aliquot of the enzyme in 50 mM Tris HCl buffer, pH 7.4, is preincubated at 37° C. for 2 minutes and the reaction is initiated by the addition of 4 nmol of r-ANF in a total volume of 50 $\mu$l. The reaction is terminated after 4 minutes with the addition of 30 $\mu$l of 0.27% trifluoroacetic acid (TFA). Forty microliters of the mixture is injected into a reverse phase-HPLC and analyzed using a C4 cartridge in a 3 minute, isocratic separation. Twenty-three percent of buffer B (0.1% TFA in 80% acetonitrile) is used. Buffer A is 0.1% TFA in water. One unit of activity is defined as the hydrolysis of 1 nmol of r-ANF per minute at 37° C. at pH 7.4. $IC_{50}$ values for inhibition of the enzyme are determined, i.e. the concentration of test compound required for 50% inhibition of the hydrolysis of ANF.

The test compound is dissolved in dimethyl sulfoxide or 0.25M sodium bicarbonate solution, and the solution is diluted with pH 7.4 buffer to the desired concentration.

In vitro testing is most appropriate for the free mercapto carboxylic acids of the invention.

Illustrative of the invention, trans 3-mercaptomethyl-2-oxo-1-azacyclodecane-10-carboxylic acid demonstrates an $IC_{50}$ of about 3 nM in the GAAP in vitro assay. Similar values are obtained in the rat-ANF in vitro assay.

The effect of the compounds of the invention on rat plasma ANF concentration can be determined as follows:

Male Sprague-Dawley rats (275-390 g) are anesthetized with ketamine (150 mg/kg)/acepromazine (10%) and instrumented with catheters in the femoral artery and vein to obtain blood samples and infuse ANF, respectively. The rats are tethered with a swivel system and are allowed to recover for 24 hours before being studied in the conscious, unrestrained state.

In this assay, plasma ANF levels are determined in the presence and absence of NEP inhibition. On the day of study, all rats are infused continuously with ANF at 450 ng/kg/min. i.v. for the entire 5 hours of the experiment. Sixty minutes after beginning the infusion, blood samples for baseline ANF measurements are obtained (time 0) and the rats are then randomly divided into groups treated with the test compound or vehicle. Additional blood samples are taken 30, 60, 120, 180 and 240 minutes after administration of the test compound.

Plasma concentrations are determined by a specific radioimmunoassay. The plasma is diluted ($\times 12.5$, $\times 25$ and $\times 50$) in buffer containing: 50 mM Tris (pH 6.8), 154 mM NaCl, 0.3% bovine serum albumin, 0.01% EDTA. One hundred microliters of standards [rANF (99–126)] or samples are added to 100 $\mu$l of rabbit anti-rANF serum and incubated at 4° C. for 16 hours. Ten thousand cpm of [$^{125}$I]rANF are then added to the reaction mixture which is incubated at 4° C. for an additional 24 hours. Goat anti-rabbit IgG serum coupled to paramagnetic particles is added to the reaction mixture and bound [$^{125}$I]rANF is pelleted by exposing the mixture to an attracting magnetic rack. The supernatant is decanted and the pellets counted in a gamma counter. All determinations are performed in duplicate. Plasma ANF levels are expressed as a percent of those measured in vehicle-treated animals which received ANF alone (450 ng/kg/min i.v.).

Illustrative of the invention, N-[[trans 3R,10S-3-(acetylthiomethyl)-2-oxo-1-azacyclodecan-10-yl]-carbonyl]-trans 4-hydroxy-L-proline benzyl ester at doses of about 1–10 mg/kg p.o., produces significant increases in plasma ANF levels.

The antihypertensive effect can be determined in desoxycorticosterone acetate (DOCA)-salt hypertensive rats.

DOCA-salt hypertensive rats (280–380 g) are prepared by the standard method. Rats underwent a unilateral nephrectomy and one week later are implanted with silastic pellets containing 100 mg/kg of DOCA. The rats are maintained on 1% NaCl/0.2% KCl drinking water for three to five weeks until sustained hypertension is established. The antihypertensive activity is evaluated at this time.

Two days before an experiment, the rats are anesthetized with methoxyflurane and instrumented with catheters in the femoral artery to measure arterial blood pressure. Forty-eight hours later, baseline arterial pressure and heart rate are recorded during a 1 hour period. The test compound (30 mg/kg p.o.) or vehicle is then administered and the same cardiovascular parameters are monitored for an additional 5 hours.

Illustrative of the invention, N-[[trans 3R,10S-3-(acetylthiomethyl)-2-oxo-1-azacyclodecan-10-yl]-carbonyl]-trans 4-hydroxy-L-proline benzyl ester at a dose of 30 mg/kg p.o., administered in 3% corn starch, produces a significant reduction in blood pressure in the DOCA-salt hypertensive rat model.

The potentiation of the natriuretic effect of ANF can be determined as follows:

Male Sprague-Dawley rats (280–360 g) are anesthetized with Inactin (100 mg/kg i.p.) and instrumented with catheters in the femoral artery, femoral vein and urinary bladder to measure arterial pressure, administer ANF and collect urine, respectively. A continuous infusion of normal saline (33 $\mu$l/min) is maintained throughout the experiment to promote diuresis and sodium excretion. The experimental protocol consists of an initial 15 minute collection period (designated as pre-control) followed by three additional collection periods. Immediately after completion of the pre-control period, test compound or vehicle is administered; nothing is done for the next 45 minutes. Then, blood pressure and renal measurements are obtained during a second collection period (designated control; 15 min). At the conclusion of this period, ANF is administered (1 $\mu$g/kg i.v. bolus) to all animals and arterial pressure and renal parameters are determined during two consecutive 15 minutes collection periods.

Mean arterial pressure, urine flow and urinary sodium excretion are determined for all collection periods. Blood pressure is measured with a Gould p50 pressure transducer, urine flow is determined gravimetrically, sodium concentration is measured by flame photometry, and urinary sodium excretion is calculated as the product of urine flow and urine sodium concentration.

Illustrative of the invention, N-[[trans 3R,10S-3-(acetylthiomethyl)-2-oxo-1-azacyclodecan-10-yl]-carbonyl]-4-hydroxy-L-proline benzyl ester at a dose of 30 mg/kg in polyethylene glycol 400 administered intraduodenally produces a significant potentiation of ANF-induced natriuresis.

The compounds of the invention are thus particularly useful as inhibitors of neutral endopeptidase, enhancing the potency and duration of action of atrial natriuretic peptide(s). The compounds are therefore particularly useful for the treatment of cardiovascular disorders such as hypertension, edema and salt retention, and cardiac conditions such as congestive heart failure.

In vitro inhibition of the angiotensin-converting enzyme (ACE) by certain compounds of this invention can be demonstrated by a method analogous to that given in Biochim. Biophys. Acta 293, p. 451 (1973). For example, said compounds are dissolved at about 1 mM concentration in phosphate buffer. To 100 microliters of solutions of the test compound in phosphate buffer, diluted to the desired concentration, are added 100 microliters of 5 mM hippuryl-histidyl-leucine in phosphate buffer, followed by 50 microliters of the angiotensin-converting enzyme preparation (from lungs of adult male rabbits) in Tris buffer, containing potassium and magnesium chloride, as well as sucrose. Said solutions are incubated at 37° C. for 30 minutes and combined with 0.75 ml of 0.6N aqueous sodium hydroxide to stop further reaction. Then 100 microliters of a 0.2% solution of o-phthalaldehyde in methanol are added at room temperature, and 10 minutes later 100 microliters of 6N hydrochloric acid. These samples are read against water in a spectrophotometer set at 360 nm, and the optical densities thereof estimated. They are corrected for the standard curve via a conversion factor expressing nanomoles of histidyl-leucine formed during said 30 minute incubation period. The results are plotted against drug concentration to determine the IC$_{50}$, i.e., the drug concentration which gives half the activity of the control sample containing no drug.

Inhibition of angiotensin converting enzyme is most evident in compounds of the invention wherein m in the respective formulae represents 7 and up. Illustrative of the invention, 3-mercaptomethyl-2-oxo-1-azacyclotetradecane-14-carboxylic acid has an IC$_{50}$ of about 45 nM for ACE inhibition and also an IC$_{50}$ of about 30 nM for inhibition of neutral endopeptidase (NEP).

Further illustrative of the invention is the more active diastereoisomer of (3R)-6-mercaptomethyl-5-oxo-1-thia-4-azacyclotridecane-3-carboxylic acid with IC$_{50}$ of 12 nM (ACE) and 18 nM (NEP), respectively.

The compounds of the invention can be prepared using processes described and illustrated herein. Such representative processes comprise:

(a) for compounds of formula I wherein n is 1, condensing a compound of the formula VI

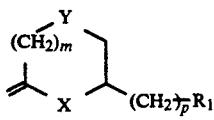

wherein Y, m, p and R$_1$ have meaning as defined hereinabove, X represents —CONH—, and in which reactive functional groups are in protected form, with a carbothioic acid of the formula VII

 (VII)

wherein R' is acyl or a salt thereof; or (b) condensing a compound of formula VIII

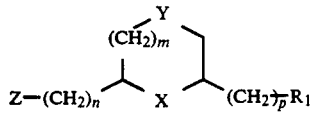

wherein Z represents hydroxyl or reactive esterified hydroxyl and wherein m, n, p, R$_1$, X and Y have meaning as defined hereinabove, with a compound of the formula VII

 (VII)

wherein R' represents acyl or a salt thereof;

(c) converting a compound of formula I so obtained wherein R$_1$ represents COOH, or reactive derivative thereof, to a compound of formula I wherein R$_1$ has any of the other meanings defined herein;
and in above said processes, if temporarily protecting any interfering reactive group(s), removing said protecting group(s), and then isolating the resulting compound of the invention; and, if desired, converting any resulting compound of the invention into another compound of the invention; and/or, if desired, converting a free carboxylic acid function into a pharmaceutically acceptable ester derivative, or converting a resulting ester into the free acid or into another ester derivative; and/or, if desired, converting a resulting free compound into a salt or a resulting salt into the free compound or into another salt, and/or, if desired, separating a mixture of isomers or racemates obtained into the single isomers or racemates, and/or, if desired, resolving a racemate obtained into the optical antipodes.

In starting compounds and intermediates which are converted to the compounds of the invention in a manner described herein, functional groups present, such as carboxyl, amino and hydroxy groups, are optionally protected by conventional protecting groups that are common in preparative organic chemistry. Protected carboxyl, amino and hydroxy groups are those that can be converted under mild conditions into free carboxyl, amino and hydroxy groups without other undesired side reaction taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (carboxyl group, amino group etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, New York 1973, T. W. Greene, "Protective Groups in Organic Synthesis", Wiley, New York 1984, and also in "The Peptides", Vol. I, Schroeder and Luebke, Academic Press, London, New York, 1965.

The condensation according to process (a) involving the condensation of a carbothioic acid of the formula VII with an exocyclic α,β-unsaturated lactam of formula VI is carried out according to methodology known in the art, e.g. with an excess of the thiol at room temperature in the presence or absence of an inert solvent, as illustrated in the examples.

The starting materials of formula VI can be prepared according to methods illustrated in the examples.

Such can be prepared, for example, starting with a ketone of formula IX

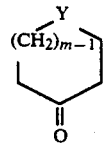

wherein Y and m have meaning as defined above by treatment with e.g. a lower alkyl ester of diazoacetic acid, in the presence of e.g. triethyloxonium tetrafluoroborate, in an inert solvent such as methylene chloride to obtain the homologous substituted cyclic ketone of the formula X

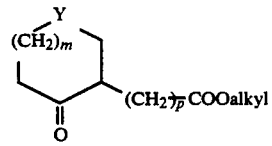

wherein p is zero, and m and y have meaning as previously defined, which is then subjected to a Schmidt reaction, e.g. with hydrazoic acid, to obtain the lactam of formula XI (as precursors for compounds of formula I wherein X=—CONH—)

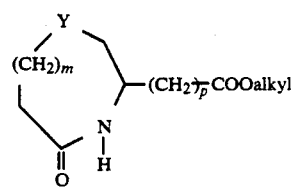

wherein p is zero and wherein m and Y have meaning as previously defined. The lactam of formula XI can then be converted to the α-bromo derivative, e.g. with bromine in the presence of phosphorus pentachloride and iodine, which can in turn be converted to the α-hydroxy derivative, e.g. with silver acetate in dimethyl formamide, followed by hydrolysis of the α-acetoxy derivative, e.g. with potassium carbonate. Oxidation of the alcohol with e.g. pyridinium chlorochromate yields an α-keto lactam of formula XII.

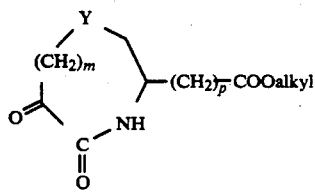
(XII)

wherein p is zero, and m and Y have meaning as defined hereinabove.

The α-keto lactam of formula XII is subsequently converted to an exocyclic α,β-unsaturated lactam of formula VI, i.e. the compound of formula XIII

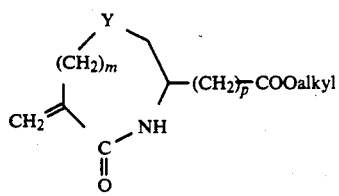
(XIII)

wherein p is zero, and m and Y have meaning as defined hereinabove by condensation first with e.g. trimethylsilylmethyl magnesium chloride, followed by reaction with boron trifluoride etherate.

The intermediate esters of formula XI through formula XIII can be hydrolyzed to the free carboxylic acid according to methods well known in the art. The acids can be subsequently homologated sequentially to yield the corresponding intermediates wherein p is 1 or 2, via an Arndt-Eistert reaction on the acid chloride, e.g. as described in J. Med. Chem. 31, 2199 (1988).

An alternate method for the preparation of starting materials of formula VI wherein p is zero and X is CONH involves the cyclization of e.g. a compound of formula XIV

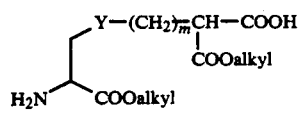
(XIV)

wherein Y and m have meaning as defined herein in the presence of an agent catalyzing amide formation, e.g. diphenylphosphoryl azide, an N,N'-disubstituted carbodiimide derivative such as N-(3-dimethylaminopropyl)-N'-ethylcarbodiimide and the like, optionally in the presence of pentafluorophenol or hydroxybenzotriazole, to obtain the lactam of formula XV

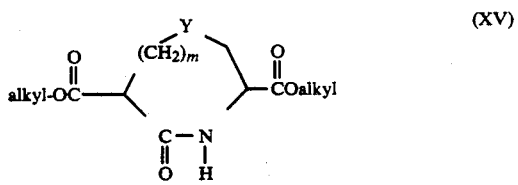
(XV)

wherein Y and m have meaning as defined hereinabove. The diester is then hydrolyzed to the lactam diacid. Subsequent condensation with paraformaldehyde in the presence of e.g. a secondary amine such as piperidine at elevated temperature, to yield a free acid corresponding to a compound of formula VI wherein $R_1$ is carboxyl, X is CONH, p is zero, and m and Y have meaning as defined herein (and corresponding to ester of formula XIII above).

The intermediates of formula XIV wherein Y represents S (sulfur) or O (oxygen) are prepared by first condensing e.g. the required omega-iodoalkylmalonate mixed ester, e.g. the t-butyl methyl ester, with an appropriate ester of cysteine or serine in the presence of a strong base, e.g. sodium methoxide. Selective hydrolysis of the t-butyl ester group with e.g. anhydrous hydrogen chloride yields the corresponding acid of formula XIV.

The intermediates of formula XIV wherein Y represents $CH_2$ are in turn prepared from a glycine derivative, e.g. N-t-BOC-glycine ethyl ester, by first condensing such with the required ω,ω'-dihaloalkane, e.g. diiodo, in the presence of a strong base, e.g. lithium diisopropyl amide to obtain the omega mono-iodo-α-aminoalkylcarboxylic acid in protected form. Subsequent condensation with a mixed malonate ester, e.g. the benzyl ethyl ester, yields the N-t-BOC triester corresponding to a compound of formula XIV which is deprotected to the compound of formula XIV using conventional benzyl ester hydrogenolysis and N-t-BOC deprotection procedure.

The preparation of a starting material of formula VI via cyclization of a compound of formula XIV is most advantageously used for larger ring compounds, e.g. wherein m is 7 or 8. The preparation of a starting material of formula VI starting from a ketone of formula IX is most advantageously used for smaller ring compounds, e.g. wherein m is 4 or 5.

The displacement according to process (b) is preferably carried out in the presence of a base as is generally known in the art for displacement of hydroxyl or reactive esterified hydroxyl by a carbothioic acid salt. In the case where Z is hydroxy, the reaction is preferably carried out in the presence of 2-fluoro-1-methyl pyridinium toluene-4-sulfonate.

Group Z being reactive esterified hydroxyl is, in particular, halo, for example bromo or iodo, also sulfonyloxy such as toluenesulfonyloxy, methanesulfonyloxy or trifluoromethanesulfonyloxy.

A starting material of formula VIII, e.g. of formula XVI

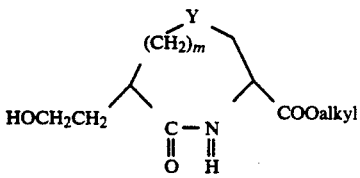

wherein m and Y have meaning as defined above can be prepared as follows:

An intermediate of formula XII (wherein p represents zero) is reacted under conditions of a Wittig type condensation with e.g. t-butyl dimethylphosphonoacetate and subsequently reduced by catalytic hydrogenation e.g. to the acetic acid ester of formula XVII

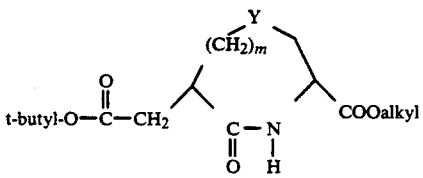

Conversion of the t-butyl ester to the free acid, of the acid to a mixed anhydride with e.g. ethyl chloroformate, and reduction thereof with sodium borohydride leads to the alcohol of formula XVI. Conversion to reactive esterified hydroxyl, e.g. halo or alkyl- or arylsulfonyloxy is carried out according to methods known in the art.

As to a starting material of formula VIII wherein Y represents -NHCO-, e.g. of formula XVIII

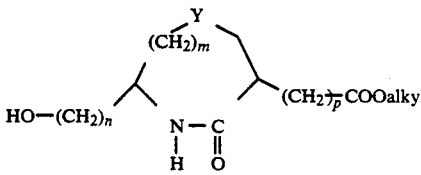

wherein for example p represents 1, such can be prepared by selective reduction of the intermediate of formula XVII with e.g. sodium borohydride in t-butanol.

As to the intermediates of formula VI or VIII, the chain length with respect to $(CH_2)_p$ or $(CH_2)_n$ can be lengthened or shortened according to methods well-known in the art. For example, a compound of formula VIII wherein Z represents e.g. halo can be reacted with an alkali metal cyanide to obtain a nitrile which can be converted to the homologous carboxylic acid.

The macrocyclic S or O containing lactam ring isomers of compounds of e.g. formula I, and derivatives thereof, can also be prepared analogously to the above-described processes. For example, cyclization of an isomeric diester of formula XIV obtained from homocysteine or homoserine yields a corresponding compound of the invention wherein the $CH_2$ group of $(CH_2)_m$ directly adjacent to Y is replaced by O or S and Y represents $CH_2$.

The compounds of the invention, e.g. of formula I wherein $R_1$ represents amides of type (a), (b), (c) or (d) as defined herein are prepared e.g. by reacting a compound of formula I wherein $R_1$ is carboxyl, or a reactive functional derivative thereof, with an amine corresponding to $R_1$ in formula I being (a), (b), (c) or (d), in optionally protected form, according to methods generally known in the art and described herein.

Reactive functional derivatives of carboxylic acids (e.g. of formula I wherein $R_1$ is carboxyl) or of intermediates, are preferably acid halides, mixed anhydrides such as the pivaloyl, alkoxycarbonyl or cyanoacetyl anhydrides.

The condensation of a required amine derivative, e.g. an amine corresponding to amide (d) or a suitable carboxy-protected amino acid derivative corresponding to amides (a) or (b) of formula I with a carboxylic acid of formula I (wherein R is acyl and $R_1$ represents carboxy) is carried out advantageously in the presence of a condensing agent such as dicyclohexylcarbodiimide or N-(3-dimethylaminopropyl)-N'-ethylcarbodiimide and hydroxybenzotriazole in an inert polar solvent such as dimethylformamide or methylene chloride, preferably at room temperature.

As to the amides of type (c), such can be prepared by condensation of an acid of formula I (wherein $R_1$ is carboxyl) with e.g. an appropriate ester of asparagine or glutamine to obtain a compound of formula I (type c), under conditions as described herein.

The amines and amino acid ester derivatives required for the above amidations are known in the art or can be prepared according to methodology known in the art. If appropriate, such an amine is an optically active or single isomer, e.g. an appropriately protected naturally occurring L-amino acid for amide derivatives of type (a), (b) or (c). Preferably a single isomer (racemate or optical antipode) of an acid of formula I (wherein $R_1$ is carboxyl) is used as starting material.

The compounds of the invention so obtained, can be converted into each other according to conventional methods. Thus, for example, resulting amides or esters may be hydrolyzed with aqueous alkalies, such as alkali metal carbonates or hydroxides, e.g. lithium hydroxide. Resulting free acids may be esterified with e.g. said unsubstituted or substituted alkanols or reactive esterified derivatives thereof such as alkyl halides, or diazoalkanes. Free acids are also converted into said metal, ammonium or acid addition salts in conventional manner.

Thus, any resulting free acid or base can be converted into a corresponding metal, ammonium or acid addition salt respectively, by reacting it with an equivalent amount of the corresponding base, basic salt, acid or ion exchange preparation, e.g. said free acids with alkali or ammonium hydroxides or carbonates, or e.g. free amines with said inorganic or organic acids respectively. Any resulting salt may also be converted into the free compound, by liberating the latter with stronger acids or bases, respectively. In view of the close relationship between the free compounds and the salts thereof, whenever a compound of the invention, or intermediate, is referred to in this context, a corresponding salt is also intended, provided such is possible or appropriate under the circumstances.

The compounds, including their salts, may also be obtained in the form of their hydrates, or include other solvents used for the crystallization. Furthermore, the functional derivatives of the free acids of formula I, wherein the carboxy group is esterified may be prepared by condensing a free acid of formula I with an esterifying agent of the formula XIX $$R_7-Z \qquad (XIX)$$

wherein Z represents hydroxy or a reactive esterified hydroxyl group; and $R_7$ represents an esterifying radical as defined herein for the carboxylic acid esters, in particular said non-aromatic radicals.

The esterification of the carboxyl group, optionally in salt form, with a compound of formula XIX wherein Z represents a reactive esterified hydroxyl group, is performed in a manner known per se, in the presence of for example an organic base, such as an organic amine, for example a tertiary amine, such as tri-lower alkylamine, for example trimethylamine, triethylamine or ethyl-di-isopropylamine, an N,N-di-lower-alkyl-aniline, for example N,N-di-methylaniline, a cyclic tertiary amine, such as an N-lower-alkylated morpholine, for example N-methyl-morpholine, a base of the pyridine type, for example pyridine, an inorganic base, for example hydroxides, carbonates, or hydrogen carbonates of alkali metals or alkaline-earth metals, for example cesium, sodium, potassium or calcium hydroxide, carbonate or hydrogen carbonate, or a quaternary ammonium base, such as a tetraalkylammonium hydroxide, carbonate or hydrogen carbonate, for example in which alkyl is e.g. methyl, ethyl, propyl, isopropyl, butyl, or the like, or an alkali metal salt of bis-trialkylsilylamide (e.g. trimethyl) optionally in the presence of a crown ether such as 18-crown-6 in a suitable inert solvent or solvent mixture, e.g. acetonitrile, toluene, and the like.

A free acid of the formula I is preferably first converted into a salt of one of the stated organic or inorganic bases, especially into the sodium or potassium salt, and is then reacted with a compound of the formula XIX. The compounds of formula XIX are known or can be prepared by methods well-known to the art.

A compound of the formula XIX wherein Z is a reactive esterified hydroxyl group can be prepared in situ. For example, a compound of the formula XIX wherein Z is chloro can be converted by treatment with sodium iodide in a solvent, for example in acetone or acetonitrile, into a compound of the formula XIX wherein Z is iodo; or esterification can be carried out with a chloro compound of the formula XIX in the presence of sodium iodide.

Esterification of a compound with a free carboxyl group using in excess an alcohol of formula XIX (wherein Z represents hydroxy) is carried out in a manner known per se, e.g. in the presence of an acid catalyst e.g. sulfuric acid or boron trifluoride etherate, preferably at an elevated termperature, advantageously ranging from about 40° C. to 100° C. Alternately, the esterification of a compound with a free carboxyl group can be carried out with at least an equimolar amount of the alcohol in the presence of a condensing agent such as dicyclohexylcarbodiimide or N-(3-dimethylaminopropyl)-N'-ethylcarbodiimide in a polar solvent such as methylene chloride, in the presence of a base if required, e.g. such as 4-(dimethylamino)pyridine.

Conversely, carboxylic acid esters can be converted to compounds of the invention with a free carboxy group using methods and conditions generally known in the art and illustrated herein. Depending on type of ester involved, useful reagents include aqueous acids or bases; also anhydrous reagents such as trialkylsilyl halides, hydrobromic acid in glacial acetic acid and hydrogen chloride in methylene chloride; also hydrogen and a hydrogenolysis catalyst. For instance, benzyl esters can be hydrogenolyzed with e.g. hydrogen in the presence of a catalyst such as palladium on charcoal; t-butyl esters can be hydrolyzed with e.g. anhydrous hydrogen chloride, other esters can be generally hydrolyzed with aqueous acid or base.

In the case mixtures of steroisomers or optical isomers of the above compounds are obtained, these can be separated into the single isomers by methods in themselves known, e.g., by fractional distillation, crystallization and/or chromatography. Racemic products can be resolved into the optical antipodes, for example, by separation of diastereomeric salts thereof, e.g., for acidic compounds by fractional crystallization of d- or l-(alpha-methylbenzylamine, cinchonidine, cinchonine, quinine, quinidine, ephedrine, dehydroabietylamine, brucine or strychnine)-salts.

The compounds of the formula I can exist as either cis or trans racemic or optically active ring diastereomers, and each racemate can in turn exist as two separate optical antipodes.

The separation of the mixture of the cis and trans racemic diastereomers obtained is usually carried out by chromatographic methods known in the art and illustrated herein, e.g. by silica gel chromatography.

The separation of a racemic carboxylic acid of formula I (wherein $R_1$ is COOH) into the optical antipodes can also be accomplished via condensation thereof in protected form with e.g. an optically active alcohol or oxazolidinone derivative to yield two diasteromeric esters or amide derivatives, which can be separated by conventional chromatographic methods into the individual diastereomers from which a single enantiomeric carboxylic acid of formula I (wherein $R_1$ is carboxyl) can be obtained by e.g. hydrolysis thereof. For example, a reactive functional derivative e.g. a mixed anhydride of a racemic carboxylic acid of the formula II wherein R is acyl is condensed with (R)- or (S)-4-benzyl-2-oxazolidinone. The resulting diastereomers are then separated by chromatography and the resulting optically active free acid of formula II is then liberated by hydrolysis with base, e.g. lithium hydroxide.

In the case where Y represents sulfur, and the carboxylic acid of formula I (wherein $R_1$ is COOH) is derived from L-cysteine, a mixture of optically active cis and trans diastereomers is obtained which can be separated directly into the optically active diastereomers without any further resolution.

The above-mentioned reactions are carried out according to standard methods, in the presence or absence of diluents, preferably such as are inert to the reagents and are solvents thereof, of catalysts, alkaline or acidic condensing or said other agents respectively and/or inert atmospheres, at low temperatures, room temperature or elevated temperatures, preferably near the boiling point of the solvents used, at atmospheric or super-atmospheric pressure.

The invention further includes any variant of said processes, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being preferred.

The present invention additionally relates to the use in mammals of the compounds of the invention and their pharmaceutically acceptable, non-toxic acid addition salts, or pharmaceutical compositions thereof, as medicaments, e.g. as neutral endopeptidase inhibitors, e.g. for the treatment of cardiovascular disorders such as hypertension, edema, salt retention and congestive heart failure.

The present invention also relates to the use of the compounds of the invention for the preparation of pharmaceutical compositions especially pharmaceutical compositions having neutral endopeptidase inhibiting activity, and e.g. antihypertensive or saluretic activity.

The pharmaceutical compositions according to the invention are those suitable for enteral, such as oral or rectal, transdermal and parenteral administration to mammals, including man, for the treatment of cardiovascular disorders, such as hypertension, comprising an effective amount of a pharmacologically active compound of the invention or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salts and/or polyethyleneglycol; for tablets also c) binders, e.g. magnesium aluminum silicate, starch paste, gelatin, tragacanth, methylcellulose, sodium carboxymethylcellulose and/or polyvinylpyrrolidone; if desired, d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

A unit dosage for a mammal of about 50 to 70 kg may contain between about 1 and 50 mg of the active ingredient. The dosage of active compound is dependent on the species of warm-blooded animal (mammal), the body weight, age and individual condition, and on the form of administration.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. Optical rotations are measured at room temperature at 589 nm (D line of sodium) unless otherwise specified.

The prefixes R and S are used to indicate the absolute configuration at each asymmetric center.

EXAMPLE 1

Ethyl 3-methylidene-2-oxo-1-azacyclodecane-10-carboxylate (1.0 g, 4.18 mmol) is dissolved in thiolacetic acid (6 mL). The reaction is stirred at room temperature overnight, and the solvent is evaporated. The product is purified by silica gel chromatograph (25% ethyl acetate/hexane) to give separately the two diastereomers of ethyl 3-(acetylthiomethyl)-2-oxo-1-azacyclodecane-10-carboxylate; major trans isomer, m.p. 115°–117° C.; minor cis isomer, m.p. 179°–180° C.

The starting material is prepared as follows:

Cyclooctanone (25 g, 198 mmol) is dissolved in methylene chloride (500 mL) and the solution is cooled to 0° C. Triethyloxonium tetrafluoroborate (121.6 g, 640 mmol) is added. Ethyl diazoacetate (41.61 g, 365 mmol) is then added dropwise over 25 minutes, and the reaction is stirred at 0° C. for 4 hours. The reaction is quenched by pouring into a solution of sodium bicarbonate (160 g) in water (1.6 L) and stirring overnight. The reaction mixture is then extracted several times with methylene chloride, the combined organic layers are dried ($Na_2SO_4$), and the solvent is evaporated. The product is purified by vacuum distillation (0.2–1.0 mm Hg) and the fraction boiling between 100°–125° C. is collected to give 2-ethoxycarbonyl-cyclononanone.

2-Ethoxycarbonyl-cyclononanone (13.72 g, 64.7 mmol) is dissolved in chloroform (200 mL) and cooled to 0° C. Methanesulfonic acid (62.4 g, 650 mmol) is added, followed by sodium azide (12.68 g, 195 mmol). The reaction is stirred at room temperature for 30 minutes, and then heated to reflux for 4 hours. The reaction mixture is poured onto ice, made basic with concentrated ammonium hydroxide (pH=9), and extracted several times with methylene chloride. The combined organic layers are dried ($MgSO_4$), and the solvent is evaporated. The product is purified by silica gel chromatography (40% ethyl acetate/hexane) to give ethyl 2-oxo-1-azacyclodecane-10-carboxylate, m.p. 101°–103° C.

Ethyl 2-oxo-1-azacyclodecane-10-carboxylate (4.0 g, 17.6 mmol) is dissolved in methylene chloride (50 mL), and cooled to 0° C. Phosphorus pentachloride (3.85 g, 18.5 mmol) and iodine (0.051 g, 0.2 mmol) are added. The reaction is stirred for 15 minutes at 0° C. Then, bromine (3.10 g, 19.4 mmol) is added, and the reaction is stirred at 0° C. for 4 hours. The reaction is quenched by adding saturated sodium sulfite (until the color of excess bromine disappears), and extracted several times with methylene chloride. The combined organic layers are dried ($Na_2SO_4$), and the solvent is evaporated. The product is purified by silica gel chromatography (15% ethyl acetate/hexane) to give cis ethyl 3-bromo-2-oxo-1-azacyclodecane-10-carboxylate, m.p. 132°–134° C.

Cis ethyl 3-bromo-2-oxo-1-azacyclodecane-10-carboxylate (2.96 g, 9.67 mmol) is dissolved in dimethylformamide (30 mL). Silver acetate (6.35 g, 38 mmol) is added, and the reaction is heated to 100° C. for 3 hours. After cooling back to room temperature, the reaction is diluted with ethyl acetate (100 mL), filtered through a pad of silica gel, and the solvent is evaporated to give crude cis ethyl 3-acetoxy-2-oxo-1-azacyclodecane-10-carboxylate.

This crude product is then dissolved in ethanol (150 mL). Potassium carbonate (1.35 g, 9.67 mmol) is added, and the reaction is stirred at room temperature for 4 hours. The reaction is diluted with ethyl acetate (200 mL), filtered through a pad of silica gel, and the solvent is evaporated to give crude cis ethyl 3-hydroxy-2-oxo-1-azacyclodecane-10-carboxylate.

This crude product (1.63 g, 6.7 mmol) is dissolved in methylene chloride (70 mL), and pyridinium chlorochromate (2.89 g, 13.4 mmol) is added. The reaction is stirred at room temperature overnight, and then diluted with ethyl acetate and filtered through a pad of florisil. The product is purified by silica gel chromatography (30% ethyl acetate/hexane) to give ethyl 2,3-di-oxo-1-azacyclodecane-10-carboxylate, m.p. 71°–73° C.

Ethyl 2,3-di-oxo-1-azacyclodecane-10-carboxylate (5.02 g, 20.81 mmol) is dissolved in ether (50 mL), and cooled to 0° C. Trimethylsilylmethylmagnesium chloride (42.0 mL of a 1.0M solution in ether, 42.0 mmol) is added dropwise, the reaction is stirred at 0° C. for 20 minutes, and then heated to reflux overnight. The reaction is quenched with saturated ammonium chloride, and extracted several times with ethyl acetate. The combined organic layers are dried ($Na_2SO_4$), and the solvent is evaporated. The product is purified by silica gel chromatography (10% ethyl acetate/hexane) to give separately the two diastereomers of ethyl 3-(trimethylsilylmethyl)-3-hydroxy-2-oxo-1-azacyclodecane-10-carboxylate; major isomer, m.p. 129°–130° C.; minor isomer, m.p. 175°–177° C.

Ethyl 3-(trimethylsilylmethyl)-3-hydroxy-2-oxo-1-azacyclodecane-10-carboxylate (0.98 g, 2.98 mmol) is dissolved in methylene chloride (50 mL), and boron trifluoride etherate (1.8 mL, 15 mmol) is added. The reaction is stirred at room temperature for 26 hours. The reaction is then quenched with saturated ammonium chloride and extracted several times with methylene chloride. The combined organic layers are dried ($MgSO_4$), and the solvent is evaporated. The product is purified by silica gel chromatography (20% ethyl acetate/hexane) to give ethyl 3-methylidene-2-oxo-1-azacyclodecane-10-carboxylate, m.p. 91°–92° C.

EXAMPLE 2

(a) The trans isomer of ethyl 3-(acetylthiomethyl)-2-oxo-1-azacyclodecane-10-carboxylate (1.35 g, 4.29 mmol) is dissolved in nitrogen-degassed ethanol (30 mL). Sodium hydroxide (13.0 mL of a 1.0M aqueous solution, 13.0 mmol) is also nitrogen-degassed and then added. After stirring for 75 minutes, the reaction is quenched with 1M hydrochloric acid (15.0 mL), and the solvent is removed. The residue is partitioned between ethyl acetate and water, and the aqueous phase is thoroughly extracted with ethyl acetate. The combined organic layers are dried ($MgSO_4$), and the solvent is evaporated to give trans 3-mercaptomethyl-2-oxo-1-azacyclodecane-10-carboxylic acid, m.p. 180°–185° C., the more active neutral endopeptidase (NEP) inhibiting diastereoisomer.

(b) Similarly prepared is the cis isomer of 3-mercaptomethyl-2-oxo-1-azacyclodecane-10-carboxylic acid (the less active diastereoisomer) from the cis isomer of ethyl 3-(acetylthiomethyl)-2-oxo-1-azacyclodecane-10-carboxylate.

EXAMPLE 3

Trans 3-mercaptomethyl-2-oxo-1-azacyclodecane-10-carboxylic acid (0.75 g, 3.06 mmol) is dissolved in pyridine (20 mL). Acetyl chloride (0.26 g, 3.37 mmol) is added, and the reaction is stirred at room temperature overnight. The reaction is quenched by cooling to 0° C., adding concentrated hydrochloric acid (20 mL), diluting with water, and extracting several times with ethyl acetate. The combined organic layers are dried ($MgSO_4$), and the solvent is evaporated to give trans 3-(acetylthiomethyl)-2-oxo-1-azacyclodecane-10-carboxylic acid, MS:M+1=288.

EXAMPLE 4

Trans 3-(acetylthiomethyl)-2-oxo-1-azacyclodecane-10-carboxylic acid (1.15 g, 4.0 mmol) and 1-hydroxybenzotriazole (0.61 g, 4.0 mmol) and 4-methylmorpholine (1.32 mL, 12.0 mmol) and L-serine-t-butyl ether-t-butyl ester hydrochloride (1.02 g, 4.0 mmol) are all dissolved in methylene chloride (40.0 mL), and the reaction is cooled to 0° C. To this solution is added N-[dimethylaminopropyl]-N'-ethylcarbodiimide hydrochloride (1.54 g, 8.0 mmol), and the reaction is allowed to warm up to room temperature and stirred overnight. The solvent is then removed, and the residue is partitioned between ethyl acetate and water. After the aqueous layer is discarded, the organic layer is washed with 2.5N hydrochloric acid, saturated sodium bicarbonate, brine, dried ($NaSO_4$), and the solvent is evaporated. The product is purified by silica gel chromatography (30% ethyl acetate/hexane) to give N-[[trans 3-(acetylthiomethyl)-2-oxo-1-azacyclodecan-10-yl]-carbonyl]-L-serine-t-butyl ether-t-butyl ester (mixture of diastereomers), MS:M+1=487.

EXAMPLE 5

N-[[trans 3-(acetylthiomethyl)-2-oxo-1-azacyclodecan-10-yl]-carbonyl]-L-serine-t-butyl ether-t-butyl ester (0.87 g, 1.78 mmol) is dissolved in nitrogen-degassed ethanol (18.0 mL). An aqueous solution of 1N sodium hydroxide (3.6 mL, 3.6 mmol), also nitrogen-degassed, is added, and the reaction is stirred for 90 minutes. The reaction is quenched with 1M hydrochloric acid (5.0 mL), and partitioned between ethyl acetate and water. The aqueous layers are dried ($NaSO_4$), and the solvent is evaporated. The product is purified by silica gel chromatography (25% ethyl acetate/hexane) to give N-[[trans 3-mercaptomethyl-2-oxo-1-azacyclodecan-10-yl]-carbonyl]-L-serine-t-butyl ether-t-butyl ester (mixture of diastereomers), MS:M+1=445.

EXAMPLE 6

N-[[trans 3-mercaptomethyl-2-oxo-1-azacyclodecan-10-yl]-carbonyl]-L-serine-t-butyl ether-t-butyl ester (0.43 g, 0.97 mmol) is dissolved in methylene chloride (25.0 mL). Anhydrous hydrochloric acid gas from a lecture bottle is bubbled into the solution for 15 minutes, and the reaction is stirred for 24 hours. The solvent is evaporated to give N-[[trans 3-mercaptomethyl-2-oxo-1-azacyclodecan-10-yl]-carbonyl]-L-serine (mixture of diastereomers), MS:M+1=333.

EXAMPLE 7

Similarly prepared according to procedures described in the previous examples are:

(a) the two diastereomers and precursors of N-[[trans 3-mercaptomethyl-2-oxo-1-azacyclodecan-10-yl]-carbonyl]-L-lysine hydrochloride, by first coupling the trans isomer of 3-(acetylthiomethyl)-2-oxo-1-azacyclodecane-10-carboxylic acid with N(ε)-t-BOC-L-lysine-t-butyl ester.

(b) the two diastereometers and precursors of N-[[trans 3-mercaptomethyl-2-oxo-1-azacyclodecan-10-yl]-carbonyl]-L-proline, by coupling the trans isomer of 3-(acetylthiomethyl)-2-oxo-1-azacyclodecane-10-carboxylic acid with L-proline-t-butyl ester.

(c) a single diastereomer and precursors of N-[[trans 3-mercaptomethyl-2-oxo-1-azacyclodecan-10-yl]-carbonyl]-L-glutamic acid, by first coupling the trans isomer of 3-(acetylthiomethyl)-2-oxo-1-azacyclodecane-10-carboxylic acid with L-glutamic acid di-t-butyl ester.

(d) a mixture of diastereomers and precursors of (S)-N-[[trans 3-mercaptomethyl-2-oxo-1-azacyclodecan-10-yl]-carbonyl]-amino-succinimide, by coupling the trans isomer of 3-(acetylthiomethyl)-2-oxo-1-azacyclodecane-10-carboxylic acid with L-asparagine-t-butyl-ester.

(e) a mixture of diastereoisomers and precursors of N-[[trans 3-mercaptomethyl-2-oxo-1-azacyclodecan-10-yl]-carbonyl]-L-hydroxyproline, by first coupling the trans isomer of 3-(acetylthiomethyl)-2-oxo-1-azacyclodecane-10-carboxylic acid with L-hydroxyproline-t-butyl ether-t-butyl ester.

(f) a mixture of diastereomers and precursors of N-[[trans 3-mercaptomethyl-2-oxo-1-azacyclodecan-10-yl]-carbonyl]-L-methionine sulfone, by coupling the trans isomer of 3-(acetylthiomethyl)-2-oxo-1-azacyclodecane-10-carboxylic acid with L-methionine sulfone methyl ester, and hydrolyzing the resulting product with aqueous sodium hydroxide.

EXAMPLE 8

Trans 3-(acetylthiomethyl)-2-oxo-1-azacyclodecane-10-carboxylic acid (0.30 g, 1.05 mmol) is dissolved in tetrahydrofuran (5.0 mL). 4-Methylmorpholine (0.14 mL, 1.05 mmol) is then added, and the reaction is cooled to −20° C. Ethyl chloroformate (0.1 mL, 1.05 mmol) is then added, and the reaction is stirred at −20° C. for 30 minutes. The reaction is then filtered, and the filtrate is concentrated to give a yellow oil. This oil is dissolved in methylene chloride (20.0 mL), and anhydrous ammonia gas is bubbled through the solution for 1 hour. The bubbling is stopped, and the reaction is stirred an additional 1 hour. The solvent is evaporated, and the residue is partitioned between ethyl acetate and water. The aqueous layer is extracted several times with ethyl acetate, the combined organic layers are dried ($Na_2SO_4$), and the solvent is evaporated to give trans 3-(acetylthiomethyl)-2-oxo-1-azacyclodecane-10-carboxamide, MS:M+1=287.

EXAMPLE 9

Trans 3-(acetylthiomethyl)-2-oxo-1-azacyclodecane-10-carboxamide (0.16 g, 0.56 mmol) is dissolved in ethanol (5.0 mL). An aqueous solution of 1N sodium hydroxide (0.60 mL, 0.60 mmol) is added, and the reaction is stirred for 1 hour. The reaction is acidified with 1N hydrochloric acid to a pH of about 3, and the solvent is evaporated. The residue is partitioned between ethyl acetate and water, and the aqueous layer is extracted several times with ethyl acetate. The combined organic layers are dried ($Na_2SO_4$), and the solvent is evaporated to give trans 3-mercaptomethyl-2-oxo-1-azacyclodecane-10-carboxamide, m.p. 185°–192° C.

EXAMPLE 10

Trans 3-(acetylthiomethyl)-2-oxo-1-azacyclodecane-10-carboxylic acid (0.100 g, 0.35 mmol), 3-aminopyridine (0.036 g, 0.38 mmol), 1-hydroxybenzotriazole (0.047 g, 0.035 mmol), and 4-methylmorpholine (0.077 mL, 0.70 mmol) are dissolved in methylene chloride (2.5 mL), and the reaction is cooled to 0° C. To this solution is added N-(dimethylaminopropyl)-N'-ethylcarbodiimide hydrochloride (0.134 g, 0.70 mmol), and the reaction is allowed to warm up to room temperature and then stirred overnight. The reaction is partitioned between methylene chloride and water, the organic layer is dried ($MgSO_4$), and the solvent is evaporated. The product is purified by silica gel chromatography (70% ethyl acetate/hexane) to give 3-{N-[[trans 3-(acetylthiomethyl)-2-oxo-1-azacyclodecan-10-yl]-carbonyl]-amino}-pyridine, MS: M+1=364.

EXAMPLE 11

3-{N-[[trans 3-(acetylthiomethyl)-2-oxo-1-azacyclodecan-10-yl]-carbonyl]-amino}-pyridine (0.040 g, 0.11 mmol) is dissolved in ethanol (1.0 mL). An aqueous solution of nitrogen-degasded 1N sodium hydroxide (0.33 mL, 0.33 mmol) is added, and the reaction is stirred for 90 minutes. The reaction is quenched with 1N hydrochloric acid (0.33 mL, 0.33 mmol), and the solvent is evaporated. The residue is partitioned between ethyl acetate and water, and the aqueous layer is extracted several times with ethyl acetate. The combined organic layers are dried ($MgSO_4$), and the solvent is evaporated. The residue is dissolved in methylene chloride (5.0 mL), and anhydrous hydrochloric acid gas is bubbled through the reaction for 5 minutes. The solvent is evaporated to give 3-{N-[[trans 3-mercaptomethyl-2-oxo-1-azacyclodecan-10-yl]-carbonyl]-amino}-pyridine hydrochloride, MS: M+1=322.

EXAMPLE 12

Trans 3-(acetylthiomethyl)-2-oxo-1-azacyclodecane-10-carboxylic acid (0.15 g, 0.52 mmol), 1-acetoxy-2-aminoethane hydrochloride (0.073 g, 0.52 mmol), 1-hydroxybenzotriazole (0.12 g, 0.52 mmol), and 4-methylmorpholine (0.17 mL, 1.56 mmol) are dissolved in methylene chloride (3.0 mL), and the reaction is cooled to 0° C. To this solution is added N-(dimethylaminopropyl)-N'-ethylcarbodiimide hydrochloride (0.20 g, 1.04 mmol), and the reaction is allowed to warm up to room temperature and then stirred overnight. The reaction is diluted with more methylene chloride, and the organic layer is washed with 1N hydrochloric acid, saturated sodium bicarbonate, dried ($MgSO_4$), and the solvent is evaporated. The product is purified by silica gel chromatography (75% ethyl acetate/hexane) to give 2-acetoxy-N-[[trans 3-(acetylthiomethyl)-2-oxo-1-azacyclodecan-10-yl]-carbonyl]-ethylamine, MS: M+1=373.

The starting material is prepared as follows:

2-Aminoethanol (1.22 g, 20.0 mmol) is dissolved in acetic acid (10.0 mL) and cooled to 0° C. Acetyl chloride (2.8 mL, 40.0 mmol) is added, and the reaction is stirred at 0° C. for 15 minutes. The reaction is diluted with diethyl ether (25.0 mL), and a white solid is collected by vacuum filtration to give 1-acetoxy-2-aminoethane hydrochloride, m.p. 127°–129° C.

EXAMPLE 13

(a) 2-acetoxy-N-[[trans 3-(acetylthiomethyl)-2-oxo-1-azacyclodecan-10-yl]-carbonyl]-ethylamine (0.11 g, 0.29 mmol) is dissolved in nitrogen-degassed ethanol (2.0 mL). An aqueous solution of nitrogen-degassed 1N sodium hydroxide (0.9 mL, 0.9 mmol) is added, and the reaction is stirred for 80 minutes. The reaction is quenched by adding 1N hydrochloric acid (1.5 mL), and the solvent is evaporated. The residue is partitioned between ethyl acetate and water, and the aqueous layer is extracted several times with ethyl acetate. The combined organic layers are dried (MgSO$_4$), and the solvent is evaporated to give 2-N-[[trans 3-mercaptomethyl-2-oxo-1-azacyclodecan-10-yl]-carbonyl]-aminoethanol, m.p. 190°–196° C.

(b) Similarly prepared according to examples 12 and 13(a) is 2-[2-N-[(trans 3-mercaptomethyl-2-oxo-1-azacyclodecan-10-yl)-carbonyl]-aminoethoxy]ethanol, by coupling trans 3-(acetylthiomethyl)-2-oxo-1-azacyclodecane-10-carboxylic acid with 1-acetoxy-2-(2-aminoethoxy)ethane hydrochloride to first yield the S-acetyl derivative, followed by hydrolysis with 1N sodium hydroxide.

(c) Similarly prepared according to examples 12 and 13(a) is 3-N-[(trans 3-mercaptomethyl-2-oxo-1-azacyclodecan-10-yl)-carbonyl]amino-1-propanol, m.p. 142°–145° C., by coupling trans 3-(acetylthiomethyl)-2-oxo-1-azacyclodecane-10-carboxylic acid with 1-acetoxy-3-aminopropane hydrochloride to yield the S-acetyl derivative, followed by hydrolysis with 1N sodium hydroxide.

(d) Similarly prepared according to examples 12 and 13(a) is 2-N-methyl-N-[(trans 3-mercaptomethyl-2-oxo-1-azacyclodecan-10-yl)-carbonyl]-aminoethanol, m.p. 55°–57° C., by coupling trans 3-(acetylthiomethyl)-2-oxo-1-azacyclodecane-10-carboxylic acid with 1-acetoxy-2-methylaminoethane hydrochloride to first yield the S-acetyl derivative, followed by hydrolysis with 1N sodium hydroxide.

(e) Similarly prepared according to examples 12 and 13(a) is N-[(trans 3-mercaptomethyl-2-oxo-1-azacyclodecan-10-yl)-carbonyl]-diethanolamine, by coupling trans 3-(acetylthiomethyl)-2-oxo-1-azacyclodecane-10-carboxylic acid with di-(2-acetoxyethyl)amine hydrochloride to first yield the S-acetyl derivative, followed by hydrolysis with 1N sodium hydroxide.

EXAMPLE 14

Trans 3-(acetylthiomethyl)-2-oxo-1-azacyclodecane-10-carboxylic acid (0.15 g, 0.52 mmol) is dissolved in dimethylformamide (2.5 mL). Benzyl bromide (0.062 mL, 0.52 mmol) and cesium carbonate (0.085 g, 0.26 mmol) are added, and the reaction is stirred at room temperature overnight. The reaction is diluted with water, and the aqueous layer is extracted several times with methylene chloride. The combined organic layers are dried (MgSO$_4$), and the solvent is evaporated. The product is purified by silica gel chromatography (10% ethyl acetate/hexane) to give trans benzyl 3-(acetylthiomethyl)-2-oxo-1-aza-cyclodecane-10-carboxylate m.p. 117°–118° C.

EXAMPLE 15

(a) Trans 3-(acetylthiomethyl)-2-oxo-1-azacyclodecane-10-carboxylic acid (0.15 g, 0.52 mmol), 1-hydroxybenzotriazole (0.070 g, 0.52 mmol), 4-methylmorpholine (0.17 mL, 1.56 mmol) and L-serine benzyl ester hydrochloride (0.120 g, 0.52 mmol) are all dissolved in methylene chloride (3.0 mL), and the reaction is cooled to 0° C. To this solution is added N-(dimethylaminopropyl)-N'-ethylcarbodiimide hydrochloride (0.20 g, 1.04 mmol), and the reaction is allowed to warm up to room temperature and stir overnight. The reaction is diluted with more methylene chloride, and the organic layer is washed with 1N hydrochloric acid, saturated sodium bicarbonate, dried (MgSO$_4$), and the solvent is evaporated. The product is purified by silica gel chromatography (60% ethyl acetate/hexane) to give N-[[trans 3-(acetylthiomethyl)-2-oxo-1-azacyclodecan-10-yl]-carbonyl]-L-serine benzyl ester, m.p. 185°–195° C. (mixture of diastereomers).

(b) Similarly prepared is trans N-[[trans 3-(acetylthiomethyl)-2-oxo-1-azacyclodecan-10-yl]-carbonyl]-4-hydroxy-L-proline benzyl ester (mixture of diastereomers).

EXAMPLE 16

The more polar major chiral isomer of N-[[trans 3-(acetylthiomethyl)-2-oxo-1-azacyclodecan-10-yl]-carbonyl]-(R)-4-benzyl-2-oxazolidinone (1.23 g, 2.75 mmol) is dissolved in tetrahydrofuran (45.0 mL) and water (15.0 mL), and the reaction is cooled to 0° C. Lithium hydroxide hydrate (0.116 g, 2.75 mmol) is added, and the reaction is stirred at 0° C. for 45 minutes. The solvent is then evaporated, and the residue is partitioned between saturated sodium bicarbonate and methylene chloride. The aqueous layer is extracted several times with methylene chloride, and then the aqueous layer is acidified with 2.5N hydrochloric acid to pH=3. The aqueous layer is extracted several times with ethyl acetate, the combined organic layers dried (MgSO$_4$) and the solvent is evaporated, to give one enantiomer of trans 3-(acetylthiomethyl)-2-oxo-1-azacyclodecane-10-carboxylic acid, m.p. 144°–145° C.; $[\alpha]_D + 88.36°$ (c=6.9 mg/ml, CH$_2$Cl$_2$), which is assigned the 3R, 10S configuration.

The starting material is prepared as follows:

Trans 3-(acetylthiomethyl)-2-oxo-1-azacyclodecane-10-carboxylic acid (2.90 g, 10.1 mmol) is dissolved in tetrahydrofuran (45.0 mL), triethylamine (1.48 mL, 10.2 mmol) is added, and the reaction is cooled to −78° C. Pivaloyl chloride (1.31 mL, 10.2 mmol) is added, the reaction is warmed to 0° C., stirred for 3 hours, and then cooled down again to −78° C. Meanwhile, in a separate flask, (R)-4-benzyl-2-oxazolidinone (1.88 g, 10.2 mmol) is dissolved in tetrahydrofuran (35 mL) and cooled to −78° C.; butyl lithium (6.63 mL of a 1.6M solution in hexane, 10.2 mmol) is added and the reaction is stirred at −78° C. for 30 minutes. This oxazolidinone anion is then cannulated into the first reaction flask, which is stirred at −78° C. for an additional 1 hour, and then allowed to warm up to room temperature and stir overnight. The reaction is quenched with saturated ammonium chloride, and all of the solvent is evaporated. The product is purified by an initial silica gel chromatography (50% ethyl acetate/hexane) to give n-[[trans 3-(acetylthiomethyl)-2-oxo-1-azacyclodecan-10-yl]-carbonyl]-(R)-4-benzyl-2-oxazolidinone as a mixture of two chiral diastereomers. These diastereomers are then separated by another silica gel chromatography (15% ether/40% hexane/45% methylene chloride) to yield the less polar (minor) chiral isomer, and the more polar (major) chiral isomer, m.p. 65°–66° C., $[\alpha]_D + 10.97°$ (c=7.52 mg/ml, CH$_2$Cl$_2$) leading to the more active NEP inhibiting enantiomer.

EXAMPLE 17

The enantiomer of trans 3-(acetylthiomethyl)-2-oxo-1-azacyclodecane-10-carboxylic acid of Example 16 (0.15 g, 0.52 mmol) is dissolved in nitrogen-degassed ethanol (3.5 mL). Nitrogen-degassed sodium hydroxide (1.5 mL of a 1N aqueous solution, 1.5 mmol) is added and the reaction is stirred at room temperature for 90 minutes. The reaction is quenched by adding 1N hydrochloric acid (1.6 mL), and the solvent is evaporated. The residue is triturated with water, and the precipitate is collected by filtration to give the pure enantiomer of trans 3-mercaptomethyl-2-oxo-1-azacyclodecane-10-carboxylic acid (0.089 g), m.p. 213°–215° C.; $[\alpha]_D+48.56°$ (c=4.3 mg/ml, EtOH), which is assigned the 3R, 10S configuration.

EXAMPLE 18

(a) The enantiomer of trans 3-(acetylthiomethyl)-2-oxo-1-azacyclodecane-10-carboxylic acid of Example 16(0.30 g, 1.04 mmol), 1-hydroxybenzotriazole (0.141 g, 1.04 mmol), 4-methylmorpholine (0.287 mL, 2.60 mmol), and trans L-hydroxyproline benzyl ester hydrochloride (0.269 g, 1.04 mmol) are dissolved in methylene chloride (22.0 mL), and the reaction is cooled to 0° C. To this solution is added N-[dimethylaminopropyl]-N'-ethylcarbodiimide hydrochloride (0.400 g, 2.08 mmol), and the reaction is allowed to warm up to room temperature and stirred overnight. The reaction is diluted with more methylene chloride, and the organic layer is washed with 1N hydrochloric acid, saturated sodium bicarbonate, dried (MgSO$_4$), and the solvent is evaporated. The product is purified by silica gel chromatography (3% methanol/methylene chloride) to give the pure enantiomer of N-[[trans 3-(acetylthiomethyl)-2-oxo-1-azacyclodecan-10-yl]-carbonyl]-trans-4-hydroxy-L-proline benzyl ester, m.p. 145° C.; $[\alpha]_D+4.36°$ (c=8.9 mg/ml, CH$_2$Cl$_2$) which is assigned the 3R, 10S configuration.

(b) Similarly prepared is the corresponding enantiomer of N-[[trans 3-(acetylthiomethyl)-2-oxo-1-azacyclodecan-10-yl]-carbonyl]-L-serine benzyl ester.

(c) Similarly prepared is the corresponding enantiomer of N-[[trans 3-(acetylthiomethyl)-2-oxo-1-azacyclodecan-10-yl]-carbonyl]-L-proline benzyl ester.

EXAMPLE 19

(a) The enantiomer of trans 3-(acetylthiomethyl)-2-oxo-1-azacyclodecane-10-carboxylic acid of Example 16(0.23 g, 0.80 mmol), 1-hydroxybenzotriazole (0.11 g, 0.80 mmol), 4-methylmorpholine (0.22 mL, 2.0 mmol), and L-hydroxyproline ethyl ester hydrochloride (0.16 g, 0.80 mmol) are dissolved in methylene chloride (5.0 mL), and the reaction is cooled to 0° C. To this solution is added N-[dimethylaminopropyl]-N'-ethylcarbodiimide hydrochloride (0.31 g, 1.60 mmol), and the reaction is allowed to warm up to room temperature and stirred overnight. The reaction is diluted with more methylene chloride, and the organic layer is washed with 1N hydrochloric acid, saturated sodium bicarbonate, dried (MgSO$_4$), and the solvent is evaporated. The product is purified by silica gel chromatography (80% ethyl acetate/hexane) to give N-[[trans 3-(acetylthiomethyl)-2-oxo-1-aza-cyclodecan-10-yl]-carbonyl]-trans 4-hydroxy-L-proline ethyl ester as a single enantiomer, $[\alpha]_D+5.73°$ (c=4.1 mg/ml, CH$_2$Cl$_2$) which is assigned the 3R, 10S configuration.

(b) Similarly prepared is the corresponding enantiomer of N-[[trans 3-(acetylthiomethyl)-2-oxo-1-azacyclodecan-10-yl]-carbonyl]-L-serine ethyl ester.

(c) Similarly prepared is the corresponding enantiomer of N-[[trans 3-(acetylthiomethyl)-2-oxo-1-azacyclodecan-10-yl]-carbonyl]-L-proline ethyl ester.

(d) Similarly prepared is trans N-[[trans 3-(acetylthiomethyl)-2-oxo-1-azacyclodecan-10-yl]-carbonyl]-trans 4-hydroxy-L-proline 5-indanyl ester.

EXAMPLE 20

(a) Trans N-[[trans 3-(acetylthiomethyl)-2-oxo-1-azacyclodecan-10-yl]-carbonyl]-4-hydroxy-L-proline ethyl ester, the enantiomer of Example 19a (0.137 g, 0.32 mmol) is dissolved in nitrogen-degassed ethanol (2.5 mL). Nitrogen-degassed sodium hydroxide (1.0 mL of a 1M aqueous solution, 1.0 mmol) is added, and the reaction is stirred at room temperature for 90 minutes. The reaction is quenched by adding 1N hydrochloric acid (1.1 mL) and the solvent is evaporated. The residue is partitioned between ethyl acetate and water, the aqueous layer is extracted well with ethyl acetate, dried (MgSO$_4$), and the solvent is evaporated to give the pure enantiomer of trans N-[[trans 3-mercaptomethyl-2-oxo-1-azacyclodecan-10-yl]-carbonyl]-4-hydroxy-L-proline, m.p. 128°–130° C., $[\alpha]_D-50.30°$ (c=4.5 mg/ml, EtOH) which is assigned the 3R, 10S configuration.

(b) Similarly prepared is the corresponding enantiomer of N-[[trans 3-mercaptomethyl-2-oxo-1-azacyclodecan-10-yl]-carbonyl]-L-serine;

(c) Similarly prepared is the corresponding enantiomer of N-[[trans 3-mercaptomethyl-2-oxo-1-azacyclodecan-10-yl]-carbonyl]-L-proline.

EXAMPLE 21

3-t-Butoxycarbonylmethyl-10-hydroxymethyl-2-oxo-1-azacyclodecane (0.50 g, 1.67 mmol) is dissolved in acetone (5.0 mL) and benzene (5.0 mL). Triethylamine (0.26 mL, 1.9 mmol) is added, followed by 2-fluoro-1-methylpyridinium toluene-4-sulfonate (0.54 g, 1.9 mmol), and the reaction is stirred at room temperature for 90 minutes. Thiolacetic acid (0.14 mL, 1.9 mmol) and more triethylamine (0.26 mL, 1.9 mmol) are added, and the reaction is heated to reflux for 2 hours. The solvent is then removed, the crude product is partitioned between methylene chloride and water, and the aqueous phase is extracted several times with methylene chloride. The combined organic layers are dried (MgSO$_4$) and the solvent is evaporated. The crude product is purified by silica gel chromatography (15% ethyl acetate/hexane) to give 10-(acetylthiomethyl)-3-t-butoxycarbonylmethyl-2-oxo-1-azacyclodecane, MS: M+1=358.

The starting material is prepared as follows:
Potassium hexamethyldisilylamide (40.5 mL of a 0.58M solution in toluene, 23.5 mmol) is added to THF (60 mL), and then cooled to 0° C. t-Butyl dimethylphosphonoacetate (4.6 mL, 23.5 mmol) is added dropwise, and the reaction is warmed to room temperature and stirred for 25 minutes. Ethyl 2,3-di-oxo-1-azacyclodecane-10-carboxylate (2.83 g, 11.74 mmol) is added in THF (15 mL), and the reaction is stirred at room temperature for 2.5 hours. The reaction is quenched with saturated ammonium chloride, and then extracted several times with ethyl acetate. The combined organic layers are dried (MgSO$_4$), and the solvent is evaporated. The product is purified by silica gel chromatography (30% ethyl acetate/hexane) to give ethyl 3-t-butoxycarbonylmethylidene-2-oxo-1-azacyclodecane-10-carboxylate.

Ethyl 3-t-butoxycarbonylmethylidene-2-oxo-1-azacyclodecane-10-carboxylate (2.85 g, 8.4 mmol) is dissolved in ethyl acetate (75 mL). 10% Pd/C (2.0 g) is added, and the reaction is stirred under an atmosphere of hydrogen for 4.5 hours. The reaction is filtered through Celite, and the solvent is removed. The crude product is purified by silica gel chromatography (20% ethyl acetate/hexane) to give separately the two diastereomers of ethyl 3-t-butoxycarbonylmethyl-2-oxo-1-azacyclodecane-10-carboxylate.

The major isomer of ethyl 3-t-butoxycarbonylmethyl-2-oxo-1-azacyclodecane-10-carboxylate (0.68 g, 2.0 mmol) is dissolved in t-butanol (10 mL). Sodium borohydride (0.23 g, 6.0 mmol) is added and the reaction is warmed to 55° C. Methanol (2.0 mL) is added over a twenty minute period, and the reaction is kept at 55° C. for an additional 1 hour. The reaction is then partitioned between ethyl acetate and water, and the aqueous phase is extracted several times with ethyl acetate. The combined organic layers are dried (MgSO$_4$), and the solvent is evaporated. The crude product is purified by silica gel chromatography (50% ethyl acetate/hexane) to give 3-t-butoxycarbonylmethyl-10-hydroxymethyl-2-oxo-1-azacyclodecane, MS: M+1=300.

EXAMPLE 22

10-(Acetylthiomethyl)-3-t-butoxycarbonylmethyl-2-oxo-1-azacyclodecane (0.24 g, 0.67 mmol) is dissolved in nitrogen-degassed ethanol (5.0 mL). Sodium hydroxide (1.35 mL of a 1.0M aqueous solution) is also nitrogen-degassed and then added. The reaction is stirred at room temperature for 2 hours, and then acidified with 1N hydrochloric acid (1.6 mL). The solvent is evaporated, the crude product is partitioned between ethyl acetate and water, and the aqueous phase is extracted several times with ethyl acetate. The combined organic layers are dried (MgSO$_4$), and the solvent is evaporated to give 10-mercaptomethyl-3-t-butoxycarbonylmethyl-2-oxo-1-azacyclodecane.

10-Mercaptomethyl-3-t-butoxycarbonylmethyl-2-oxo-1-azacyclodecane (0.21 g, 0.69 mmol) is dissolved in methylene chloride (15 mL). Gaseous hydrogen chloride is bubbled through the solvent for 15 minutes, and then the reaction is sealed and stirred overnight. The solvent is evaporated the next day to give 10-mercaptomethyl-2-oxo-1-azacyclodecane-3-acetic acid, MS: M+1=260.

EXAMPLE 23

3-Methylidene-2-oxo-1-azacyclotetradecane-14-carboxylic acid (0.70 g, 2.62 mmol) is suspended in thiolacetic acid (5.0 mL), and the reaction is stirred at room temperature overnight. The solvent is evaporated to give both diastereomers of 3-(acetylthiomethyl)-2-oxo-1-azacyclotetradecane-14-carboxylic acid.

The starting material is prepared as follows:

Diisopropylamine (8.1 mL, 57.67 mmol) is dissolved in tetrahydrofuran (125.0 mL), and the solution is cooled to 0° C. Butyl lithium (36.0 mL of a 1.6M solution in hexane, 57.67 mmol) is added, and the solution is stirred at 0° C. for 30 minutes. The reaction is then cooled to −78° C., and hexamethylphophoramide (5.04 mL, 28.83 mmol) is added. A solution of N-t-BOC-glycine ethyl ester (5.85 g, 28.83 mmol) in tetrahydrofuran (125.0 mL) is added dropwise, and the reaction is stirred at −78° C. for 1 hour. A solution of 1,10-diiododecane (11.4 g, 28.83 mmol) in tetrahydrofuran (25.0 mL) is added, and the reaction is stirred at −78° C. for 1 hour. The reaction is warmed to −40° C. and stirred for an additional 1 hour. Finally, the reaction is warmed to 0° C., and quenched by adding saturated ammonium chloride. The reaction is partitioned between ether and water, the organic layer is washed with brine, dried (Na$_2$SO$_4$), and the solvent is evaporated. The product is purified by silica gel chromatography (5% ethyl acetate/hexane) to give ethyl 2-t-butoxycarbonylamino-12-iodo-dodecanoate.

Sodium hydride (0.44 g of a 50% oil dispersion, 9.11 mmol) is suspended in tetrahydrofuran (36.0 mL). Benzyl ethyl malonate (1.86 mL, 9.11 mmol) is added slowly dropwise, and the reaction is stirred at room temperature for 30 minutes. Then a solution of ethyl 2-t-butoxycarbonylamino-12-iodo-dodecanoate (4.28 g, 9.11 mmol) in tetrahydrofuran (10.0 mL) is added slowly dropwise, and the reaction is stirred overnight. The reaction is quenched by adding saturated ammonium chloride, and partitioned between ethyl acetate and water. The organic layer is washed with brine, dried (Na$_2$SO$_4$), and the solvent is evaporated. The product is purified by silica gel chromatography (10% ethyl acetate/hexane) to give diethyl 2-t-butoxycarbonylamino-13-benzyloxycarbonyl-1,14-tetradecanedicarboxylate.

Diethyl 2-t-butoxycarbonylamino-13-benzyloxycarbonyl-1,14-tetradecanedicarboxylate (5.0 g, 8.87 mmol) is dissolved in ethyl acetate (150.0 mL), and 10% Pd-C (2.6 g) is added. The reaction flask is put under an atmosphere of hydrogen and stirred for 2 hours. The product is then filtered through a pad of Celite, and the solvent is evaporated to give diethyl 2-t-butoxycarbonylamino-13-carboxy-1,14-tetradecanedicarboxylate.

Diethyl 2-t-butoxycarbonylamino-13-carboxy-1,14-tetradecanedicarboxylate (3.98 g, 8.40 mmol) is dissolved in methylene chloride (150.0 mL), and hydrogen chloride gas is bubbled through the solution for 15 minutes. The sealed reaction is stirred for 2.5 hours, and then the solvent is evaporated to give diethyl 2-amino-13-carboxy-1,14-tetradecanedicarboxylate hydrochloride.

Diethyl 2-amino-13-carboxy-1,14-tetradecanedicarboxylate hydrochloride (0.312 g, 0.76 mmol) is dissolved in methylene chloride (152.0 mL). The reaction is cooled to 0° C. Triethylamine (0.53 mL, 3.8 mmol) is added, followed by diphenylphosphoryl azide (0.493 mL, 2.28 mmol), and the reaction is stirred at 0° C. for 66 hours. The reaction is quenched by adding saturated ammonium chloride, the organic layer is dried (Na$_2$SO$_4$), and the solvent is evaporated. The product is purified by silica gel chromatography (15% ethyl acetate/hexane) to give both diastereomers of diethyl 2-oxo-1-azacyclotetradecane-3,14-dicarboxylate.

Diethyl 2-oxo-1-azacyclotetradecane-3,14-dicarboxylate (1.14 g, 3.2 mmol; mixture of both diastereomers) is dissolved in ethanol (32.0 mL). Sodium hydroxide (9.6 mL of a 1N aqueous solution, 9.6 mmol) is added dropwise, and the solution is stirred at room temperature for 3 hours. The reaction is then acidified to pH 3 with 1N hydrochloric acid, and partitioned between ethyl acetate and water. The aqueous phase is extracted several times with ethyl acetate, the combined organic layers are dried (Na$_2$SO$_4$), and the solvent is evaporated to give both diastereomers of 2-oxo-1-azacyclotetradecane-3,14-dicarboxylic acid.

2-oxo-1-azacyclotetradecane-3,14-dicarboxylic acid (0.868 g, 2.9 mmol) is dissolved in pyridine (15.0 mL). Piperidine (0.060 mL, 0.59 mmol) is added, followed by paraformaldehyde (0.133 g, 4.43 mmol), and the reaction is heated to 65° C. for 4 hours. The reaction is then cooled to 0° C., and concentrated hydrochloric acid is added to bring the pH to approximately 2. The reaction is partitioned between ethyl acetate and water, and the aqueous phase is extracted several times with ethyl acetate. The combined organic layers are dried (Na$_2$SO$_4$), and the solvent is evaporated to give 3-methylidene-2-oxo-1-azacyclotetradecane-14-carboxylic acid.

EXAMPLE 24

3-(Acethiomethyl)-2-oxo-1-azacyclotetradecane-14-carboxylic acid (0.90 g, 2.62 mmol) is dissolved in dimethylformamide (26.0 mL). Cesium carbonate (0.427 g, 1.31 mmol) is added, followed by methyl iodide (0.163 mL, 2.62 mmol), and the reaction is stirred at room temperature overnight. The solvent is evaporated, and the reaction mixture is partitioned between ethyl acetate and water. The aqueous phase is extracted several times with ethyl acetate, the combined organic layers are dried (Na$_2$SO$_4$), and the solvent is evaporated. The product is purified by silica gel chromatography (15% ethyl acetate/hexane) to give the two separate diastereomers of methyl 3-(acetylthiomethyl)-2-oxo-1-azacyclotetradecane-14-carboxylate: major isomer, m.p. 114°-115° C.; minor more active NEP inhibiting isomer, m.p. 167°-168° C.

EXAMPLE 25

(a) Methyl 3-(acetylthiomethyl)-2-oxo-1-azacyclotetradecane-14-carboxylate (0.223 g, 0.624 mmol; major isomer) is dissolved in nitrogen-degassed ethanol (3.0 mL). Sodium hydroxide (1.9 mL of a 1N aqueous solution, 1.9 mmol) is also nitrogen-degassed and then added. The reaction is stirred at room temperature for 2 hours. The reaction is quenched by adding 1N hydrochloric acid (3.8 mL), and partitioned between ethyl acetate and brine. The organic layer is dried (na$_2$SO$_4$), and the solvent is evaporated to give 3-mercaptomethyl-2-oxo-1-azacyclotetradecane-14-carboxylic acid, m.p. 170°-172° C.

(b) Similarly prepared is the minor more active NEP inhibiting isomer of 3-mercaptomethyl-2-oxo-1-azacyclotetradecane-14-carboxylic acid, m.p. 175°-177° C., from the minor isomer of methyl 3-(acetylthiomethyl)-2-oxo-1-azacyclotetradecane-14-carboxylate.

EXAMPLE 26

(a) (3R)-6-Methylidene-5-oxo-1-thia-4-azacyclotridecane-3-carboxylic acid (1.21 g, 4.70 mmol) is suspended in thiolacetic acid (40 ml). The mixture is stirred overnight at room temperature. The solvent is evaporated at 40° C. and the residue is triturated from diethyl ether and hexane (1:1). The resulting solid is filtered and dried to give a mixture of both diastereomers of (3R)-6-(acetylthiomethyl)-5-oxo-1-thia-4-azacyclotridecane-3-carboxylic acid, m.p. 125°-130° C.

The starting material is prepared as follows:

Sodium hydride (3.04 g of a 50% oil dispersion, 127 mmol) is suspended in dimethylformamide (300 ml) and the suspension is cooled to 0° C. t-Butyl methyl malonate (20.08 g, 115 mmol) is added dropwise slowly and the reaction mixture is warmed to room temperature. 1,7-Dibromoheptane (29.75 g, 115 mmol) is added dropwise and the mixture is stirred for 3 hours. The mixture is partitioned between diethyl ether (500 ml) and water (1000 ml). The organic layer is washed with water (3×500 ml), brine (1×500 ml), dried (MgSO$_4$) and the solvent is evaporated. The product is purified by silica gel chromatography (10% ethyl acetate/hexane) to give t-butyl methyl 7-bromoheptylmalonate as an oil.

t-Butyl methyl 7-bromoheptylmalonate (8.81 g, 25.1 mmol) is dissolved in acetone (50 ml). Sodium iodide (3.7 g, 25.1 mmol) is added and the mixture is stirred at reflux for 2 hours. The reaction mixture is filtered and the filtrate is concentrated to dryness. The residue is dissolved in methylene chloride and filtered again. The filtrate is concentrated to dryness to give t-butyl methyl 7-iodoheptylmalonate as an oil.

L-Cysteine methyl ester hydrochloride (9.05 g, 52.7 mmol) is dissolved in nitogen-degassed methanol (300 ml) and solid sodium methoxide (6.11 g, 113 mmol) is added. The reaction mixture is stirred for 15 minutes at room temperature and t-butyl methyl 7-iodoheptylmalonate (15.00 g, 37.7 mmol) is added. The mixture is stirred overnight at room temperature and partitioned between diethyl ether (500 ml) and water (100 ml). The organic layer is washed with brine (300 ml), dried (MgSO$_4$) and the solvent is evaporated. The product is purified by silica gel chromatography (5% methanol/methylene chloride) to give dimethyl (2R)-2-amino-12-t-butoxycarbonyl-4-thia-1,13-tridecanedicarboxylate as an oil.

Dimethyl (2R)-2-amino-12-t-butoxycarbonyl-4-thia-1,13-tridecanedicarboxylate (3.39 g, 8.36 mmol) is dissolved in methylene chloride (50 ml) and hydrogen chloride gas is bubbled through the solution for 5 minutes. The reaction mixture is stirred for 2 hours at room temperature. The solvent is evaporated to give dimethyl (2R)-2-amino-12-carboxy-4-thia-1,13-tridecanedicarboxylate hydrochloride as an oil.

Dimethyl (2R)-2-amino-12-carboxy-4-thia-1,13-tridecanedicarboxylate hydrochloride (6.87 g, 17.8 mmol) is dissolved in methylene chloride (3500 ml) and triethylamine (9.00 g, 89 mmol) is added. 2,3,4,5,6-Pentafluorophenol (9.83 g, 53.4 mmol) is added followed by N-(3-dimethylaminopropyl)-N'-ethylcarbodiimide hydrochloride (17.06 g, 89 mmol). The reaction mixture is stirred overnight at room temperature and the solvent volume is reduced to 500 ml. The organic solution is washed with water (1×500 ml). 1N potassium hydroxide (2×500 ml), brine (1×500 ml), dried (MgSO$_4$) and concentrated to dryness. The residue is purified by silica gel chromatography (40% ethyl acetate/hexane) to give methyl (3R)-6-methoxycarbonyl-5-oxo-1-thia-4-azacycltridecane-3-carboxylate, m.p. 156°-164° C.

Methyl (3R)-6-methoxycarbonyl-5oxo-1-thia-4-azacyclotridecane-3-carboxylate (2.39 g, 7.21 mmol) is suspended in methanol (75 ml) and 1N sodium hydroxide (22.0 ml, 22.0 mmol) is added. The mixture is stirred for 4 hours at room temperature. The solvent is evaporated and the residue is dissolved in water (150 ml). The aqueous solution is adjusted to pH 1 by addition of 1N hydrochloric acid and extracted with ethyl acetate (3×100 ml). The combined extracts are washed with brine (1×100 ml), dried (MgSO$_4$) and the solvent is evaporated to give (3R)-6-carboxy-5-oxo-1-thia-4-azacyclotridecane-3-carboxylic acid, m.p. 167°-170° C.

(3R)-6-Carboxy-5-oxo-1-thia-4-azacyclotridecane -3-carboxylic acid (1.71 g, 5.64 mmol) is dissolved in pyridine (20 ml) and piperidine (0.096 g, 1.13 mmol) is added followed by paraformaldehyde (0.25 g, 8.46 mmol). The mixture is heated to 65° C. and stirred for 2 hours. The mixture is cooled to room temperature, poured into 6N hydrochloric acid (100 ml) and extracted with ethyl acetate (2×100 ml). The combined extracts are washed with brine (1×100 ml), dried (MgSO₄) and solvent is evaporated to give (3R)-6-methylidene-5-oxo-1-thia-4-azacyclotridecane-3-carboxylic acid, m.p. 184°–186° C.

(b) Similarly prepared is (3R)-6-(pivaloylthiomethyl)-5-oxo-1-thia-4-azacyclotridecane-3-carboxylic acid, m.p. 160°–170° C., by substituting thiolpivaloic acid for thiolacetic acid.

EXAMPLE 27

(3R)-6-(Acetylthiomethyl)-5-oxo-1-thia-4-azacyclotridecane-3-carboxylic acid (1.40 g, 4.03 mmol) is partially dissolved in methanol (50 ml) and freshly prepared ethereal diazomethane is added until a yellow color persists. The reaction is quenched with glacial acetic acid and the solvents are evaporated to give mixture of diastereomers. The residue is dissolved in methylene chloride (100 ml) and washed with saturated sodium bicarbonate (1×100 ml), brine (1×100 ml), dried (Na₂SO₄) and the solvent is evaporated. The product is purified by silica gel chromatography (30% ethyl acetate/hexane) to give the two separate diastereomers of methyl (3R)-6-(acetylthiomethyl)-5-oxo-1-thia-4-azacyclotridecane-3-carboxylate: Isomer A, m.p. 156°–161° C.; Isomer B, m.p. 199°–201° C.

EXAMPLE 28

(a) Methyl (3R)-6-(acetylthiomethyl)-5-oxo-1-thia-4-azacyclotridecane-3-carboxylate (Isomer B) (0.16 g, 0.44 mmol) is partially dissolved in nitrogen degassed tetrahydrofuran (10 ml) and water (5 ml). Lithium hydroxide monohydrate (0.056 g, 1.33 mmol) is added and the mixture is stirred at room temperature for 3 hours. The mixture is poured into 1N hydrochloric acid and extracted with ethyl acetate (2×50 ml). The combined organic layers are washed with brine (1×50 ml), dried (Na₂SO₄) and the solvent is evaporated to give (3R)-6-mercaptomethyl-5-oxo-1-thia-4-azacyclotridecane-3-carboxylic acid (Isomer B), m.p. 169°–173° C.; the more active NEP inhibiting isomer.

(b) (3R)-6-Mercaptomethyl-5-oxo-1-thia-4-azacyclotridecane-3-carboxylic acid (Isomer A) is prepared in a similar manner, m.p. 181°–184° C.

EXAMPLE 29

Ethyl (3R)-6-methylidene-5-oxo-1-thia-4-azacyclotridecane-3-carboxylate (0.11 g, 0.37 mmol) is suspended in thiolacetic acid (5 ml) and the mixture is stirred for 48 hours at room temperature. The solvent is evaporated and the product is triturated from diethyl ether/hexane (1:1). The desired diastereomer is obtained by silica gel chromatography (10% ethyl acetate/hexane) to give ethyl (3R)-6-(acetylthiomethyl)-5-oxo-1-thia-4-azacyclotridecane-3-carboxylate, m.p. 193°–196° C.

The starting material is prepared as follows:

(3R)-6-Methylidene-5-oxo-1-thia-4-azacyclotridecane-3-carboxylic acid (0.16 g), 0.62 mmol) is dissolved in ethanol (5 ml) and hydrogen chloride gas is bubbled through the solution for 5 minutes. The solution is stirred overnight at room temperature and the solvent is evaporated to give ethyl (3R)-6-methylidene-5-oxo-1-thia-4-azacyclotridecane-3-carboxylate, m.p. 146°–147° C.

EXAMPLE 30

(a) (3R)-6-(Acetylthiomethyl)-5-oxo-1-thia-4-azacyclotridecane-3-carboxylic acid (0.62 g, 1.78 mmol) is dissolved in dimethylformide (8 ml) and cesium carbonate (0.64 g, 1.96 mmol) is added, followed by benzyl bromide (0.31 g, 1.78 mmol). The mixture is stirred overnight at room temperature, poured into water (300 ml) and extracted with ethyl acetate (2×100 ml). The combined organic layers are washed with water (2×100 ml), brine (1×200 ml), dried (MgSO₄) and the solvent is evaporated. Silica gel chromatography (5% ethyl acetate/hexane) gives benzyl (3R)-6-(acetylthiomethyl)-5-oxo-1-thia-4-azacyclotridecane-3-carboxylate, m.p. 192°–193° C.

(b) (3R)-6-(Pivaloylthiomethyl)-5-oxo-1-thia-4-azacyclotridecane-3-carboxylic acid (0.25 g, 0.64 mmol) is dissolved in dimethylformamide (5 ml) and cesium carbonate (0.23 g, 0.71 mmol) is added, followed by benzyl bromide (0.11 g, 0.64 mmol). The mixture is stirred overnight at room temperature, poured into water (300 ml) and extracted with ethyl acetate (2×100 ml). The combined organic layers are washed with water (2×100 ml), brine (1×200 ml), dried (MgSO₄) and the solvent is evaporated. Silica gel chromatography (3% ethyl acetate/hexane) gives benzyl (3R)-6-(pivaloylthiomethyl)-5-oxo-1-thia-4-azacyclotridecane-3-carboxylate, m.p. 135°–137° C.

EXAMPLE 31

(3R)-6-(Pivaloylthiomethyl)-5-oxo-1-thia-4-azacyclotridecane-3-carboxylic acid (0.17 g, 0.44 mmol) is dissolved in methylene chloride (5 ml) and trans-4-hydroxy-L-proline benzyl ester hydrochloride (0.14 g, 0.52 mmol) is added, followed by triethylamine (0.053 g, 0.52 mmol). N-(3-dimethylaminopropyl)-N'-ethylcarbodiimide hydrochloride (0.10 g, 0.52 mmol) is added and the mixture is stirred at room temperature overnight. The organic solution is washed with water (30 ml), brine (30 ml), dried (MgSO₄) and the solvent is evaporated. The product is purified by silica gel chromatography (5% methanol/methylene chloride) to give a diastereomeric mixture of trans-N-[[3R-6-(pivaloylthiomethyl)-5-oxo-1-thia-4-azacyclotridecan-3-yl]-carbonyl]-4-hydroxy-L-proline benzyl ester, m.p. 66°–70° C.

EXAMPLE 32

Trans-N-[(3R)-6-(pivaloylthiomethyl)-5-oxo-1-thia-4-azacyclotridecan-3-yl-carbonyl]-4-hydroxy-L-proline benzyl ester (0.30 g, 0.05 mmol) is dissolved in nitrogen degassed tetrahydrofuran (1 ml) and water (0.5 ml). Lithium hydroxide monohydrate (0.006 g, 0.15 mmol) is added and the mixture is stirred at room temperature for 2.5 hours. The mixture is poured into 1N hydrochloric acid and extracted with ethyl acetate (2×10 ml). The combined organic layers are dried (MgSO₄) and the solvent is evaporated. The product is triturated from diethyl ether to give trans N-[[(3R)-6-mercaptomethyl-5-oxo-1-thia-4-azacyclotridecan-3-yl]-carbonyl]-4-hydroxy-L-proline, m.p. 124°–130° C.

EXAMPLE 33

(3R)-6-(Acetylthiomethyl)-5-oxo-1-thia-4-azacyclotetradecane-3-carboxylic acid, m.p. 123°–127° C., is prepared in a manner analogous to (3R)-6-(acetylthiomethyl)-5-oxo-1-thia-4-azacyclotridecane-3-carboxylic acid (example 26), starting with 1,8-dibromooctane instead of 1,7-dibromoheptane.

EXAMPLE 34

(3R)-6-(Acetylthiomethyl)-5-oxo-1-thia-4-azacyclotetradecane-3-carboxylic acid (0.53 g, 1.53 mmol) is dissolved in dimethylformamide (10 ml) and cesium carbonate (0.55 g, 1.68 mmol) is added. Benzyl bromide (0.26 g, 1.53 mmol) is added and the mixture is stirred overnight at room temperature. The mixture is poured into water (300 ml) and extracted with ethyl acetate (2×50 ml). The combined organic layers are washed with water (2×100 ml), brine (1×100 ml), dried ($Na_2SO_4$) and the solvent is evaporated. The product is purified by silica gel chromatography (5% ethyl acetate/methylene chloride) to give two separate diastereomers of benzyl (3R)-6-(acetylthiomethyl)-5-oxo-1-thia-4-azacyclotetradecane-3-carboxylate. Isomer A, m.p. 159°–162° C.; Isomer B, m.p. 174°–178° C.

EXAMPLE 35

(a) Benzyl (3R)-6-(acetylthiomethyl)-5-oxo-1-thia-4-azacyclotetradecane-3-carboxylate (Isomer A), (0.11 g, 0.25 mmol) is dissolved in nitrogen degassed tetrahydrofuran (5 ml) and water (1 ml). Lithium hydroxide monohydrate (0.032 g, 0.75 mmol) is added and the mixture is stirred for 3 hours at room temperature. The mixture is poured into 1N hydrochloric acid and extracted with ethyl acetate (2×50 ml). The combined organic layers are washed with brine (1×50 ml), dried ($MgSO_4$) and the solvent is evaporated. The product is triturated from diethyl ether/hexane (1:1) to give (3R)-6-mercaptomethyl-5-oxo-1-thia-4-azacyclotetradecane-3-carboxylic acid (Isomer A), m.p. 165°–168° C.

(b) (3R)-6-Mercaptomethyl-5-oxo-1-thia-4-azacyclotetradecane-3-carboxylic acid (Isomer B), m.p. 200°–203° C., the more active NEP inhibiting isomer, is prepared in a similar manner.

EXAMPLE 36

The following compounds can be prepared similarly to procedures described in the previous examples.

(a) 3-mercaptomethyl-4-oxo-1-thia-5-azacyclodecane-6-carboxylic acid, e.g. starting from 1-thiacyclooctan-4-one.

(b) 6-mercaptomethyl-5-oxo-1-thia-4-azacyclodecane-3-carboxylic acid, e.g. starting from 1-thiacyclooctan-4-one.

(c) N-[[6-(acetylthiomethyl)-5-oxo-1-thia-4-azacyclotetradecan-3-yl]-carbonyl]-trans 4-hydroxy-L-proline benzyl ester.

(d) 6-(acetylthiomethyl)-5-oxo-1-oxa-4-azacyclotridecane-3-carboxylic acid, prepared e.g. similarly to the corresponding 1-thia compound using e.g. L-serine methyl ester as starting material.

EXAMPLE 37

Preparation of 1,000 capsules each containing 30 mg of the active ingredient, as follows:

| | |
|---|---:|
| N-[[trans-3R,10S-3-(acetylthiomethyl)-2-oxo-1-azacyclodecane-10-yl]-carbonyl]-trans 4-hydroxy-L-proline benzyl ester | 30.00 g |
| Lactose | 187.00 g |
| Modified starch | 80.00 g |
| Magnesium stearate | 3.00 g |

Procedure: All the powders are passed through a screen with openings of 0.6 mm. The drug substance is placed in a suitable mixer and mixed first with the magnesium stearate, then with the lactose and starch until homogenous. No. 2 hard gelatin capsules are filled with 300 mg of said mixture each, using a capsule filling machine.

Analogously capsules are prepared, containing about 10–100 mg of the other compounds disclosed and exemplified herein.

What is claimed is:

1. A compound of the formula

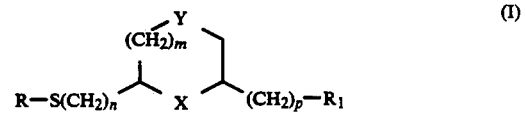
(I)

wherein R is hydrogen or acyl; m is an integer from 4 to 9 inclusive; n is 1 or 2; p is zero, 1 or 2; X is —CONH— or —NHCO—; Y is S or O; $R_1$ is —COOH; or $R_1$ is

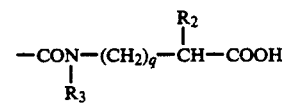

in which $R_2$ is hydrogen, lower alkyl, aryl-lower alkyl, amino-lower alkyl, hydroxy-lower alkyl, acyloxy-lower alkyl, lower alkoxy-lower alkyl, mercapto-lower alkyl, lower alkyl-(thio, sulfinyl or sulfonyl)-lower alkyl, or carboxy-lower alkyl, $R_3$ is hydrogen or lower alkyl, and q is zero or an integer from 1 to 5 inclusive; or $R_1$ is

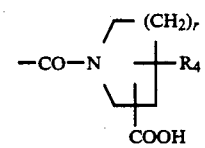

in which $R_4$ is hydrogen, lower alkyl, lower alkoxy, hydroxy or acyloxy, and r is 1 or 2; or $R_1$ is

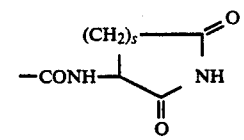

in which s is 1 or 2; or $R_1$ is

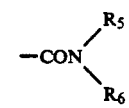

in which $R_5$ and $R_6$ independently represent hydrogen, lower alkyl, $C_5$- or $C_6$-cycloalkyl, (hydroxy-, acyloxy or lower alkoxy-) lower alkyl, carbocyclic or heterocyclic monocyclic aryl, or (hydroxy-, acyloxy- or alkoxy-) lower alkyloxy-lower alkyl; or $R_5$ and $R_6$ together with the nitrogen to which they are attached represent pyrrolidino, piperidino, morpholino, piperazino or N-alkylpiperazino; or a macrocyclic sulfur or oxygen containing lactam ring isomer in which a $CH_2$ group of $(CH_2)_m$ in formula I is replaced by O or S, and Y represents CH$_2$; and in the above definitions, aryl is carbocyclic or heterocyclic aryl; carbocyclic aryl is phenyl or phenyl substituted by lower alkyl, hydroxy, lower alkoxy, lower alkanoyloxy, halogen, cyano, trifluoromethyl, lower alkanoylamino or lower alkoxycarbonyl; or carbocyclic aryl is naphthyl or naphthyl substituted by lower alkyl, lower alkoxy or halogen; heterocyclic aryl is thienyl, thienyl substituted by lower alkyl, pyridyl, pyridyl substituted by lower alkyl, halogen or cyano, furanyl or furanyl substituted by lower alkyl; acyl is lower alkanoyl, carbocyclic aryl-lower alkanoyl, aroyl, lower alkoxycarbonyl or aryl-lower alkoxycarbonyl; and aroyl is benzoyl or benzoyl substituted by lower alkyl, lower alkoxy, halogen or trifluoromethyl; or a pharmaceutically acceptable prodrug ester of any above said compound with a free carboxyl group; or a pharmaceutically acceptable salt of any said compound with a free acid or basic salt forming group.

2. A compound according to claim 1 wherein X is —CONH—.

3. A compound according to claim 2 wherein Y is S.

4. A compound according to claim 2 wherein p is zero.

5. A compound according to claim 2 wherein Y is S; and p is zero.

6. A compound according to claim 2 of the formula

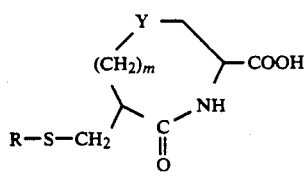

wherein R represents hydrogen or acyl; m is an integer from 4 to 9 inclusive; Y is S; or a pharmaceutically acceptable ester thereof; or a pharmaceutically acceptable salt thereof.

7. A compound according to claim 6 wherein m is 4, 7 or 8.

8. A compound according to claim 2 of the formula

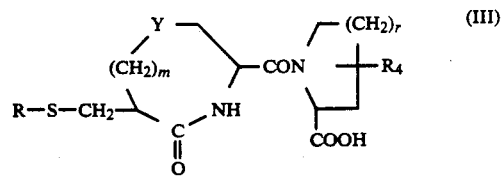

wherein m is an integer from 4 to 9 inclusive; Y is S; r is 1 or 2; R is hydrogen or acyl; R$_4$ is hydrogen, lower alkyl, lower alkoxy, hydroxy or acyloxy; or a pharmaceutically acceptable ester thereof; or a pharmaceutically acceptable salt thereof.

9. A compound according to claim 2 of the formula

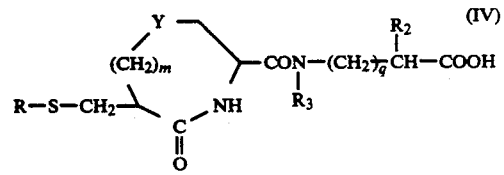

wherein m is an integer from 4 to 9 inclusive; q is zero or an interger of 1 to 5; Y is S; R is hydrogen or acyl; R$_2$ is hydrogen, lower alkyl, aryl-lower alkyl, amino-lower alkyl, hydroxy-lower alkyl, acyloxy-lower alkyl, alkoxy-lower alkyl, mercapto-lower alkyl, lower alkyl-(thio, sulfinyl or sulfonyl)-lower alkyl or carboxy-lower alkyl; R$_3$ is hydrogen or lower alkyl; or a pharmaceutically acceptable ester thereof; or a pharmaceutically acceptable salt thereof.

10. A compound according to claim 2 which is 6-mercaptomethyl-5-oxo-1-thia-4-azacyclotridecane-3-carboxylic acid or the S-acetyl derivative; a pharmaceutically acceptable ester thereof; or a pharmaceutically acceptable salt thereof.

11. A neutral endopeptidase inhibiting pharmaceutical composition comprising an effective neutral endopeptidase inhibiting amount of a compound of claim 1 in combination with one or more pharmaceutically acceptable carriers.

12. A method of treating cardiovascular disorders which comprises administering to a mammal in need of such treatment an effective neutral endopeptidase inhibiting amount of a compound of claim 1 in combination with one or more pharmaceutically acceptable carriers.

* * * * *